(12) United States Patent
Karunaratne et al.

(10) Patent No.: US 9,795,322 B1
(45) Date of Patent: Oct. 24, 2017

(54) METHODS AND SYSTEMS FOR MONITORING POSTURE WITH ALERTS AND ANALYTICS GENERATED BY A SMART SEAT COVER

(71) Applicant: Calcey Technologies (Pvt.) Ltd., Colombo (LK)

(72) Inventors: Mangalanath Wickramanayake Karunaratne, Pannipitiya (LK); Rashmi Suganda Mendis, Kalutara (LK); Sasanka Ushani Kudagoda, Kalutara (LK); Ganidu Ashen Madapatha, Pannipitiya (LK); Uswatta Liyanage Mudith Jayanuwan Uswatta, Kohuwala (LK); Asela Indika Mahathma Arachchi, Piliyandala (LK)

(73) Assignee: Right Posture Pte. Ltd., singapore (SG)

( * ) Notice: Subject to any disclaimer, the term of this patent is extended or adjusted under 35 U.S.C. 154(b) by 0 days.

(21) Appl. No.: 15/489,699

(22) Filed: Apr. 17, 2017

Related U.S. Application Data

(60) Provisional application No. 62/408,415, filed on Oct. 14, 2016.

(51) Int. Cl.
*A61B 5/00* (2006.01)
*A61B 5/11* (2006.01)
(Continued)

(52) U.S. Cl.
CPC ............ *A61B 5/1116* (2013.01); *A47C 7/004* (2013.01); *A47C 7/006* (2013.01); *A47C 7/425* (2013.01);
(Continued)

(58) Field of Classification Search
CPC ....... A61B 5/11; A61B 5/1116; A61B 5/1118; A61B 5/1123; A61B 5/742; A61B 5/7271;
(Continued)

(56) References Cited

U.S. PATENT DOCUMENTS

| 5,570,301 A | 10/1996 | Barrus |
| 6,392,550 B1 | 5/2002 | Najor |

(Continued)

FOREIGN PATENT DOCUMENTS

| DE | 4021240 A1 | 1/1992 |
| DE | 102007003762 A1 | 7/2008 |

(Continued)

OTHER PUBLICATIONS

Mutlu, Bilge, et al., "Robust, Low-Cost, Non-Intrusive Sensing and Recognition of Seated Postures," Carnegie Mellon University website, available at http://repository.cmu.edu/cgi/viewcontent.cgi?article=1040&context=hcii, accessed on Mar. 23, 2017.

(Continued)

*Primary Examiner* — Max Hindenburg
(74) *Attorney, Agent, or Firm* — American Patent Agency PC; Daniar Hussain; Xiaomeng Shi

(57) ABSTRACT

Disclosed are methods and systems for monitoring and correcting sitting posture of a user and for discouraging sedentary behavior. The system comprises a processor, a portable seat cover with embedded pressure sensors and an angle sensor, a notification device, and a non-transitory storage medium for storing program code. The program code, when executed by the processor, causes the processor to initiate an idleness timer to count how long the user has been sitting, monitor the user's sitting posture by receiving real-time sensor measurements; identify a sitting posture by applying a posture identification rule, generate a posture (Continued)

correction notification through the notification device if the identified sitting posture is not ergonomically correct, determine whether a sedentary threshold has been reached and generate a stand notification if the sedentary threshold has been reached. Embodiments of the present invention help improve sitting posture and reduce sedentary behavior to minimize associated adverse health effects.

17 Claims, 30 Drawing Sheets

(51) Int. Cl.
    *A47C 7/42*     (2006.01)
    *A47C 7/62*     (2006.01)
    *A47C 7/00*     (2006.01)
    *A47C 7/54*     (2006.01)

(52) U.S. Cl.
    CPC .................. *A47C 7/54* (2013.01); *A47C 7/62* (2013.01); *A61B 5/6891* (2013.01); *A61B 5/7271* (2013.01); *A61B 5/742* (2013.01); *A61B 2560/0223* (2013.01)

(58) Field of Classification Search
    CPC ....... A61B 5/6891; A47C 7/004; A47C 7/006; A47C 7/54; A47C 7/62; A47C 7/425
    See application file for complete search history.

(56) References Cited

U.S. PATENT DOCUMENTS

| | | | |
|---|---|---|---|
| 7,470,231 B2 | 12/2008 | Fujita et al. | |
| 7,664,546 B2 | 2/2010 | Hartley et al. | |
| 8,477,039 B2 | 7/2013 | Gleckler et al. | |
| 8,558,702 B2 * | 10/2013 | Smith | A61B 5/00 340/573.1 |
| 9,196,175 B2 * | 11/2015 | Walsh | A61B 5/4561 |
| 9,286,782 B2 | 3/2016 | Chang et al. | |
| 2010/0010380 A1 | 1/2010 | Panken et al. | |
| 2010/0298661 A1 | 11/2010 | McCombie | |
| 2015/0015399 A1 | 1/2015 | Gleckler et al. | |
| 2016/0113583 A1 | 4/2016 | Min | |
| 2016/0183687 A1 | 6/2016 | Hoyt et al. | |

FOREIGN PATENT DOCUMENTS

| | | |
|---|---|---|
| EP | 2957193 A1 | 12/2015 |
| WO | WO2003100741 A1 | 12/2003 |
| WO | WO2008119106 A1 | 10/2008 |
| WO | WO2010085826 A1 | 8/2010 |
| WO | WO2013010040 A1 | 1/2013 |

OTHER PUBLICATIONS

Andreoni, Giuseppe, et al., "Method for the analysis of posture and interface pressure of car drivers," Applied Ergonomics 33 (2002), 511-522.

Toledo, Selene Atenea Mota, "Automated Posture Analysis for Detecting Learner's Affective State," SourceTV wikipedia page on the Valve Developer Community website, available at http://developer.valvesoftware.com/wiki/Source_TV, accessed on Mar. 23, 2017.

Laerhoven, K. Van, et al., "Sustained logging and discrimination of sleep postures with low-level, wrist-worn sensors," Proceedings of IEEE 12th International Symposium on Wearable Computers (ISWC), pp. 69-76, Pittsburgh, PA, US, Sep.-Oct. 2008.

Wong, Wai Yin, et al., "Clinical Applications of Sensors for Human Posture and Movement Analysis: A Review," Prosthetics and Orthotics International v. 31, No. 1 (2007), pp. 62-75.

Cheng, Jingyuan, "Smart Chair: What Can Simple Pressure Sensors under the Chairs' Legs Tell Us about User Activity?" Proceedings of the Seventh International Conference on Mobile Ubiquitous Computing, Systems, Services and Technologies (UBICOMM-13), Sep. 29-Oct. 3, 2013, Porto, Portugal, IARIA XPS Press.

* cited by examiner

1200

| | SENSOR READINGS |
|---|---|
| 1 | UBR < X1 AND UBL < X2 |
| 2 | UBL - UBR > X3 |
| 3 | UBR - UBL > X4 |
| 4 | LB < X5 |
| 5 | BL < X6 AND BR < X7 |
| 6 | BL - BR > X8 |
| 7 | BR - BL > X9 |
| 8 | LL - LR > X10 |
| 9 | LR - LL > X11 |
| 10 | ANG > X12 |
| 11 | BL < X13 AND BR < X14 AND LB < 15 AND UBL - UBR > X16 |
| 12 | BL < X17 AND BR < X18 AND LB < X19 AND UBR - UBL > X20 |
| 13 | BL < X21 AND BR < X22 AND LB < X23 AND UBR < X24 AND UBL < X25 |
| 14 | LL - LR > X26 AND LB < X27 AND UBR < X28 AND UBL < X29 |
| 15 | LR - LL > X30 AND LB < X31 AND UBR < X32 AND UBL < X33 |
| 16 | LL - LR > X34 AND LB < X35 AND UBL - UBR > X36 |
| 17 | LR - LL > X37 AND LB < X38 AND UBL - UBR > X39 |
| 18 | LR - LL > X40 AND LB < X41 AND UBR - UBL > X42 |
| 19 | LL - LR > X43 AND LB < X44 AND UBR - UBL > X45 |
| 20 | LB < X46 AND BL < X47 AND BR < X48 AND ANG > X49 |
| 21 | LB < X50 AND UBR - UBL > X51 |
| 22 | LB < X52 AND UBL - UBR > X53 |
| 23 | LB < X54 AND UBR < X55 AND UBL < X56 |
| 24 | BL < X57 AND BR < X58 AND LB < X59 |
| 25 | LL - LR > X60 AND UBR < X61 AND UBL < X62 |
| 26 | LR - LL > X63 AND UBR < X64 AND UBL < X65 |
| 27 | LL - LR > X66 AND UBL - UBR > X67 |
| 28 | LL - LR > X68 AND UBR - UBL > X69 |
| 29 | LR - LL > X70 AND UBL - UBR > X71 |
| 30 | LR - LL > X72 AND UBR - UBL > X73 |
| 31 | LL - LR > X74 AND LB < X75 |
| 32 | LR - LL > X76 AND LB < X77 |
| 33 | LL - LR > X78 AND ANG > X79 |
| 34 | LR - LL > X80 AND ANG > X81 |
| 35 | ANG > X82 AND LB < X83 |
| 36 | BL < X84 AND BR < X85 AND ANG > X86 |
| 37 | Conditions 1-36 are not met |

FIG. 12

METHODS AND SYSTEMS FOR MONITORING POSTURE WITH ALERTS AND ANALYTICS GENERATED BY A SMART SEAT COVER

REFERENCE TO RELATED APPLICATIONS

This application is a non-provisional of and claims the benefit of provisional application having U.S. Ser. No. 62/408,415, filed on 14 Oct. 2016, and entitled "Methods and Systems for Smart Seat Cover and App to Monitor Posture with Alerts and Analytics," the entire disclosure of which is hereby incorporated by reference in its entireties herein.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the U.S. Patent and Trademark Office files or records, but otherwise reserves all copyright and trade dress rights whatsoever.

FIELD OF THE INVENTION

Embodiments of the present invention are in the field of health tracking and training, and pertain particularly to methods and systems for posture monitoring and improvement.

BACKGROUND OF THE INVENTION

The statements in the background of the invention are provided to assist with understanding the invention and its applications and uses, and may not constitute prior art.

Although the human body is designed for regular movements, today, many spend the bulk of their day sitting. Sitting for extended periods of time can cause many health complications, so much so that the phrase "sitting is the new smoking" has taken root in pop culture. Such health complications may be classified into two major categories.

First, sitting is a sedentary lifestyle with long-term effects on internal organs and the brain. For example, sitting at a desk for too long may cause anxiety, cardiovascular diseases, migraines, colon cancer, depression, diabetes, high blood pressure, obesity, and even osteoporosis. People prone to such a sedentary lifestyle may come from all age groups and professions, including office workers, students, truck drivers, and many others. Second, many sit with bad postures that can lead to strained muscles and a plethora of orthopedic issues such as back pain, disk damages, and unbalanced hips. Hunching, slouching, leg-crossing, swayed back, and pelvic tilt are all problematic postures that over time can severely impact one's orthopaedic health and quality of life, to name just a few.

To help reduce the health hazards of extended sitting, many ergonomic solutions have been developed over the years. However, current solutions available in the market mainly target bad postures by detecting and correcting such postures using smart chairs having embedded sensors or using wearable devices. A smart chair may use a large number of sensors to constantly monitor a user's posture. Several issues exist for smart chairs. For one, a smart chair is an additional or extra piece of furniture. For two, due to their bulkiness and thus lack of portability, several smart chairs may have to be purchased by the same user to accommodate multiple work locations. For three, every time the smart chair hardware or firmware is upgraded by the manufacturer, the whole chair may have to be replaced. On the other hand, while wearable devices have the advantage of portability, their posture detection capabilities may be limited. For example, a wearable sensor may look at only a tilt of the upper body in the anterior-posterior direction, without any sensing in the medial-lateral direction. Wearables may also be uncomfortable. Whether strapped on the body or clipped on a shirt, wearables are necessarily in constant contact with the body. Moreover, conventional smart chairs and wearable devices generally do not provide historical data tracking or behavioural tracking, and thus fail to monitor postures over time to help the user improve.

It would therefore be an advancement in the state of the art to provide systems and methods for monitoring postures over time and in real-time, without compromising user comfort while also providing portability and ease of use. It would further be an advancement in the state of the art to provide systems and methods for monitoring sedentary behavior over time and in real-time.

It is against this background that the present invention was developed.

BRIEF SUMMARY OF THE INVENTION

The inventors of the present invention have created methods and systems for smart seat cover and app to monitor posture with alerts and analytics.

More specifically, in one aspect, one embodiment of the present invention is a system for monitoring and correcting sitting posture of a user, and for discouraging sedentary behavior of the user. The system comprises a processor having access to a clock; a portable seat cover comprising a backrest portion and a seat portion, adapted for attachment to a chair; a plurality of sensors embedded in the portable seat cover and each having access to the processor, including at least three pressure sensors embedded in the backrest portion for monitoring shoulder and lower back positions of the user, at least one angle sensor embedded in the backrest portion for monitoring an inclination of the backrest portion relative to the seat portion, and at least two pressure sensors embedded in the seat portion for monitoring leg positions of the user; a notification device attached to the portable seat cover and having access to the processor; and a non-transitory physical storage medium for storing program code and accessible by the processor. The program code when executed by the processor, causes the processor to initiate an idleness timer to count how long the user has been sitting, where the idleness timer is activated when the user sits on the seat portion of the portable seat cover, and deactivated when the user stands up from sitting on the seat portion of the seat cover; monitor the user's sitting posture by receiving, at discrete intervals in real-time, a first plurality of sensor measurement values from the plurality of sensors; identify a sitting posture of the user by applying a posture identification rule to the first plurality of sensor measurement values, wherein the posture identification rule is based on the user's weight; determine whether the sitting posture is ergonomically correct by identifying a category that the sitting posture belongs to; in response to determining that the sitting posture is not ergonomically correct, generate a posture correction notification through the notification device to alert the user to correct the sitting posture; determine whether a sedentary threshold has been reached by comparing the idleness timer to the sedentary threshold; and in response to determining that the sedentary threshold has been reached, generate a stand notification through the notification device to alert the user to stand up.

In some embodiments of the present invention, the program code when executed by the processor, further causes the processor to initiate a stand timer to count how long the user has been standing, where the stand timer is activated when the user stands up from sitting on the seat portion of the seat cover, and deactivated when the user sits on the seat portion of the seat cover; determine whether the user has stood up in response to the stand notification; in response to determining that the user has not stood up in response to the stand notification, reduce the idleness timer by a predetermined amount of time; in response to determining that the user has stood up in response to the stand notification, pause the idleness timer until the user is seated again, increase the stand timer by the amount of time the user stood, and determine whether a standing time threshold has been reached by comparing the stand timer to the standing time threshold; in response to determining that the standing time threshold has been reached, reset the idleness timer and the stand timer; in response to determining that the standing time threshold has not been reached, reduce the idleness timer by a predetermined amount of time and reset the stand timer.

In some embodiments of the present invention, the plurality of sensors comprises at least four pressure sensors embedded in the seat portion for monitoring leg positions of the user. In some embodiments of the present invention, the stand notification comprises making the seat uncomfortable to sit in, and generating a reminder alert for display on a user device. In some embodiments of the present invention, the posture correction notification comprises an action selected from the group consisting poking the user at one or more locations on the portable seat cover, vibrating a portion of the portable seat cover, generating a reminder alert for display on a user device, generating sitting posture information for display on the user device, and sending a notification to the user device.

In some embodiments of the present invention, the program code when executed by the processor, further causes the processor to receive height and weight information of the user; and calibrate the system by instructing the user to sit in a calibration posture; and receiving a plurality of calibration sensor measurement values from the plurality of sensors, wherein the posture identification rule is based on the plurality of calibration sensor measurement values.

In some embodiments of the present invention, the program code when executed by the processor, further causes the processor to generate, for display on a user device, sitting posture information based on the first plurality of sensor measurement values, wherein the sitting posture information indicates whether one or more sensors are measuring values within an ergonomic range; receive a second plurality of sensor measurement values from the plurality of sensors; determine whether a posture change has occurred by comparing the second plurality of sensor measurement values to the first plurality of sensor measurement values; in response to determining that a posture change has occurred, generate, for display on a user device, updated sitting posture information based on the second plurality of sensor measurement values.

In some embodiments of the present invention, the program code when executed by the processor, further causes the processor to timestamp the first plurality of sensor measurement values and the identified sitting posture; and send the timestamped first plurality of sensor measurement values and/or the timestamped sitting posture to a user device, wherein the user device later uploads the timestamped first plurality of sensor measurements values and/or the timestamped sitting posture to a cloud server, when an upload connection becomes available.

In some embodiments of the present invention, the system further comprises a user device having access to the processor, wherein the user device performs a social gamification function selected from the group consisting of causing the processor to generate a posture correction notification in response to receiving a poke request from a friend, updating a posture challenge score according to the sitting posture, uploading timestamped historical posture data received from the processor to a community database, and causing the processor to update the sedentary threshold based on a group goal or a peer-to-peer goal received from the community database.

In some embodiments of the present invention, the program code when executed by the processor, further causes the processor to identify a stress level of the user based on sitting posture movement patterns.

In another aspect, the present invention is a non-transitory, computer-readable storage medium storing program code or executable instructions, which when executed by a processor, causes the processor to perform a process for monitoring and correcting sitting posture of a user, and for discouraging sedentary behavior of the user, the executable instructions causing the processor to perform the aforementioned steps.

In another aspect, the present invention is a system for monitoring and correcting sitting posture of a user, and for discouraging sedentary behavior of the user, the system comprising a user device having a processor, a display, and a first memory; a server comprising a second memory and a data repository; a telecommunications link between the user device and the server; and computer codes embodied on the first and second memories of the user-device and the server, the computer codes when executed cause the server and the user device to execute a process comprising the aforementioned steps.

In yet another aspect, the present invention is a computerized server comprising at least one processor, memory, and computer codes embodied on the memory, the computer codes when executed cause the processor to execute a process comprising the aforementioned steps.

Yet other aspects and embodiments of the present invention include the methods, processes, and algorithms comprising the steps described herein, and also include the processes and modes of operation of the systems and servers described herein. Other aspects and embodiments of the present invention will become apparent from the detailed description of the invention when read in conjunction with the attached drawings.

BRIEF DESCRIPTION OF THE DRAWINGS

Embodiments of the present invention described herein are exemplary, and not restrictive. Embodiments will now be described, by way of examples, with reference to the accompanying drawings. In these drawings, each identical or nearly identical component that is illustrated in various figures is represented by a like reference character. For purposes of clarity, not every component is labeled in every drawing. The drawings are not necessarily drawn to scale, with emphasis instead being placed on illustrating various aspects of the techniques, systems, and devices described herein.

FIG. 12 is a table illustrating exemplary posture identification rules based on various sensor measurement values, according to one embodiment of the present invention.

DETAILED DESCRIPTION OF THE INVENTION

Illustrative Definitions

Figure 1:
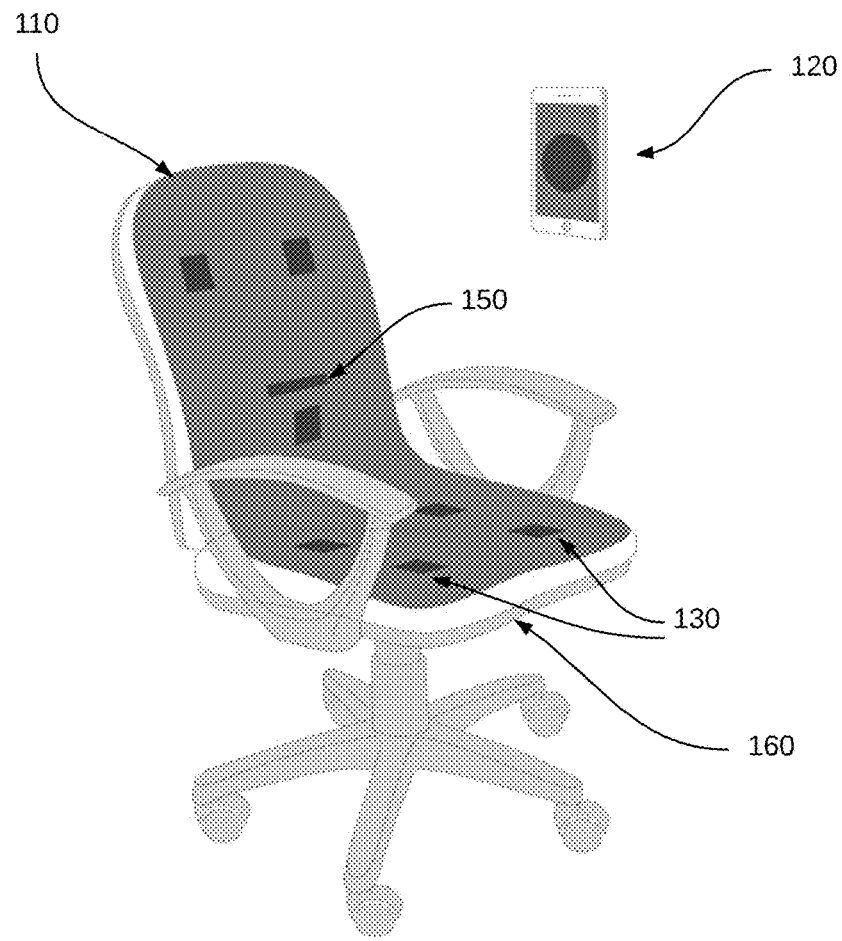
FIG. 1 is an illustrative figure showing a smart seat cover for monitoring and correcting sitting posture, according to one embodiment of the present invention.

Some illustrative definitions are provided to assist in understanding the present invention, but these definitions are not to be read as restricting the scope of the present invention. The terms may be used in the form of nouns, verbs or adjectives, within the scope of the definitions.

"SEAT" generally refers to a place, surface, area, or structure designed for an individual to sit on and to support the individual in a sitting position. Exemplary types of seats include, but are not limited to, chairs, stools, benches, car seats, sofas, couches, folding seats, ottomans, and many other structures suitable for sitting. A "CHAIR" generally refers to a seat with a back, back support, or backrest portion. A "STOOL" generally refers to a seat without any armrest or back support. Moreover, a "SEAT PORTION" may refer to the part of a chair, sofa, or the like, on which an individual may sit. A seat portion of a seat cover also refers the part of the seat cover on which the individual may sit.

"CORRECT POSTURE", "CORRECT SITTING POSTURE", "CORRECT SITTING POSITION", "IDEAL POSTURE", "IDEAL SITTING POSTURE", and "IDEAL SITTING POSITION" are ergonomically acceptable sitting positions that keep the body in alignment, decrease abnormal stress on ligaments and joints, and allow efficient use of muscles. Such ergonomically acceptable sitting positions help prevent strain and overuse of joints, ligaments, muscles, the spine and pelvic bones, and help avoid or minimize backache, neck pain, muscle pain, and many other adverse health effects. For example, one correct posture is to sit with back straight, shoulders back and relaxed, and hips positioned far back on the chair with weight distributed evenly on both hips. In embodiments of the present invention, an "ideal sitting position" for a user may be quantified, and described in terms of acceptable ranges or thresholds for sensor measurement values, and such acceptable ranges or thresholds may be obtained via automated profiling of the user's body type, and may be customized through a calibration process.

"INCORRECT SITTING POSTURE" and "INCORRECT SITTING POSITION" are ergonomically incorrect positions that deviate significantly from correct sitting positions. In embodiments of the present invention, such deviations may be quantified, and measured in terms of sensor readings that fall outside of acceptable ranges or fall below or above certain thresholds.

"ENGAGED" pressure sensors are active pressure sensors that report non-negligible measurement values. Such measurement values may fall into ergonomically acceptable ranges that define correct sitting postures. Measurements from engaged pressure sensors may also exceed certain activation thresholds. "DISENGAGED" pressure sensors are either deactivated, or activated but measure negligible pressure values. For example, a disengaged pressure sensor may report a measurement value that falls below an activation threshold. In another example, a pressure sensor situated below one leg may become disengaged when the user crosses this leg over the other, thus making the two legs unbalanced, and making the pressure value measured by this sensor fall into a negligible range that is much smaller than the value measured by another sensor situated below the other leg.

"IDLENESS TIMER" is a timer that counts how long a user has been sitting. Such an idleness timer may be activated manually or automatically. For example, it may be turned on or off through a physical switch, or electronically through a toggle on a control interface of a user device. In some embodiments, an idleness timer may be activated when the user sits on the seat portion of a smart seat cover, and may be deactivated when the user stands up from sitting on the seat portion of the smart seat cover.

"STAND TIMER" is a timer that counts how long a user has been standing. Such a stand timer may be activated manually or automatically. For example, it may be turned on or off through a physical switch, or electronically through a toggle on a control interface of a user device. In some embodiments, a stand timer may be activated when the user stands up from sitting on the seat portion of a smart seat cover, and deactivated when the user sits on the seat portion of the smart seat cover.

"CORRECT POSTURE SCORE" is a metric for measuring how good a user's sitting posture is. There may be different ways of computing a correct posture score. For example, a user may earn P amount of points when he or she has been sitting with a correct posture for a minimum period of time Q. Some postures may worth more than others. In some embodiments, a correct posture score may be linearly related to a correct sitting time, which may be the amount of time for which the user has been sitting correctly. Such a correct posture score may start to be cumulated once the correct sitting time exceeds a given threshold. In some embodiments, longer correct sitting times may weigh more. Thus, proportionally more points may be added non-linearly to the correct posture score for increasing correct sitting times.

"SEDENTARY BEHAVIOR" and "IDLE BEHAVIOR" both refer to the behavior of sitting for extended periods of time, with or without correct or good sitting postures, and with or without standing breaks.

Overview

With reference to the definitions above and the figures provided, embodiments of the present invention are now described in detail.

In the following description, for purposes of explanation, numerous specific details are set forth in order to provide a thorough understanding of the invention. It will be apparent, however, to one skilled in the art that the invention can be practiced without these specific details. In other instances, structures, devices, activities, and methods are shown using schematics, use cases, and/or flow diagrams in order to avoid obscuring the invention. Although the following description contains many specifics for the purposes of illustration, anyone skilled in the art will appreciate that many variations and/or alterations to suggested details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

Broadly, embodiments of the present invention relate to a posture monitoring system having a portable smart seat cover with embedded sensors for collecting posture and other health metrics to help improve the general overall health of a user. While referred to as a "seat cover", such a portable seat cover may comprise a backrest portion in addition to a seat portion, and may be adapted for attachment to different types of furniture for sitting, such as chairs, sofas, couches, car seats, benches, and the like. Such a smart system may further comprise other embedded electronics such as processors, memories, actuators, notification devices, communication modules and the like, to perform data processing functions, to enable its corporation with various user devices, and to further integrate into Internet of Things (IoT), and social networks.

Unlike conventional systems for posture monitoring, the present invention provides a non-intrusive, portable system with high sensitivity, high accuracy, real-time feedback, and historical data analysis capabilities. While the human body is designed for regular movements, today, many sit for extended periods of time without regular exercises and have an overall sedentary lifestyle. There are many health hazards associated with a sedentary lifestyle, such as cardiovascular disease, colon cancer, diabetes, high blood pressure, obesity, and osteoporosis, to name just a few. Moreover, people often sit with bad or incorrect postures such as hunching, leaning, slouching, leg-crossing, swayed back, pelvic tilt, and many others. Such bad postures are associated with a host of undesirable health issues such as back pain, neck strain, joint stiffness, even lumbar disc herniation. To help reduce the health hazards of extended sitting, many ergonomic solutions have been developed over the years. However, current solutions available in the market mainly target bad postures by detecting and correcting sitting postures using smart chairs with embedded sensors or using wearable devices. Several issues exist for smart chairs. For one, a smart chair is an additional or extra piece of furniture. For two, due to their bulkiness and thus lack of portability, several smart chairs may have to be purchased by the same user to accommodate multiple work locations. For three, every time the smart chair hardware or firmware is upgraded by the manufacturer, the whole chair may have to be replaced. On the other hand, while wearable devices have the advantage of portability, their posture detection capabilities may be limited. For example, a wearable sensor may look at only a tilt of the upper body in the anterior-posterior direction, without any sensing in the medial-lateral direction. Wearables may also be uncomfortable. Whether strapped on the body or clipped on a shirt, wearables are necessarily in constant contact with the body. Moreover, conventional smart chairs and wearable devices generally do not provide historical data tracking or behavioural tracking, and thus fail to monitor postures over time to help the user improve.

The posture monitoring system as disclosed herein provides the advantages of both smart chair systems and wearable devices, while offering other new and novel functionalities. More specifically, the posture monitoring system or smart seat cover system as disclosed herein comprises a portable smart seat cover having embedded pressure sensors, angle sensors, and a processor having access to a clock. This smart seat cover system may also comprise one or more notification devices, such as a buzzer, a vibration device, or an electric shock device. Structurally, the smart seat cover may comprise a backrest portion and a seat portion, and may be adapted with attachment means for securing it to a chair, for monitoring and correcting a sitting posture of a user. The backrest portion and the seat portion may be part of a contiguous arrangement, or may be two separate components held together by another attachment means. In some embodiments, the system may further comprise health sensors that monitor health indicators such as heart rate, blood pressure, and various hormone levels, and behavioural sensors, which may, independently or together with the health sensors, monitor stress levels as well as other salient behavioural features. In some embodiments, the system may include Bluetooth or other wireless communication components for communicating with a user device, a system server, or a cloud server. In some embodiments, the smart seat cover system may comprise a user device having a client application that may be accessed by the user to provide notifications and alerts, to track progresses in posture improvement, and to access posture monitoring and improvement gamification features, with or without taking part in larger online user communities or social networks.

One feature of the present invention is the intelligent placement and configuration of sensors for data collection, and robust rules for posture identification. Different embodiments of the present invention may comprise any number of pressure sensors, angle sensors, and health sensors. For example, seven pressure sensors may be placed to measure around the shoulder, lower back, hip, and leg areas, while an angle sensor may be placed in the backrest portion to measure an inclination of the upper body. Abnormal or imbalanced sensor readings may indicate different types or categories of incorrect postures. Through new and novel posture identification processes, embodiments of the present invention can distinguish among different incorrect postures with high accuracy and sensitivity, thus pin-pointing exact changes needed for posture improvements.

Another feature of the present invention is its ability to detect multiple postures while being non-intrusive in its setup. Once activated, embedded pressure sensors may detect pressure readings at different points on the smart seat cover, and an angle sensor may detect the tilt of the backrest portion with respect to the seat portion, all without interfering with the user's activities. Using sophisticated decision rules based on such sensor measurements, the processor may determine whether a user is seated with a correct posture, and if not, how exactly he or she is sitting incorrectly. Such a smart seat cover system is highly accurate with configurable sensitivities, as it correlates measurements from multiple sensors for decision making. Such a smart seat cover system is also barely noticeable during use, as it neither needs to be attached to the user's body which may cause discomfort, nor needs to be adjusted or reset frequently like many wearable devices do. Upon detecting incorrect sitting postures beyond a configurable time period, the smart seat cover system may actuate an alert via a notification device to remind the user to change his or her posture. Depending on the user's preferences, such an alert may be sent via audio or silent vibrations, pinches, or even electric shocks. Again, such automatic notifications do not interfere with the user's activities, while providing constant, real-time feedback to ensure that posture improvements occur continuously but also progressively. Moreover, in some embodiments, the smart seat cover system may perform behaviour detection over time via health sensors and behavioural sensors to monitor health metrics that may collectively indicate the user's general state of health.

Another feature of the present invention that makes the system more effective is real-time visual feedback, as enabled by quick data transmission to a user device via a wireless communication link. In some embodiments, an associated user device such as a smart phone or a tablet may periodically receive sensor data from the smart seat cover, and may run a dedicated application or web interface for visualizing the user's current sitting position in real-time, and for alerting the user to change his or her sitting position, in addition to or in place of audio or vibrational alerts. For example, the user device may display a diagram of engaged and disengaged sensors to inform the user whether his or her posture is balanced, and what adjustment to the current posture should be made. A real-time alert may also be generated when the user has been sitting for longer than a pre-configured time period. For example, the user device may play a small soothing music clip when it is time for the user to take a stand break. Moreover, all measured data from the sensors may be recorded in memory or transferred to a cloud server via the user device, and such historical data may be statistically analyzed for medical prediction and diagnostics. Coupled with real-time visual feedback, the user device may further provide gamification features such as taking on performance challenges and setting performance goals, and social features such as ranking and participating in group challenges. Such gamification and social features may make the posture monitoring and correction process more interactive and fun, thus motivate the user to participate more, and improve sitting postures over time.

Features of the smart seat cover system as discussed above offer many advantages. In addition to its high accuracy, sensitivity, and non-intrusiveness, the smart seat cover system is also portable and easy to use, since it can be simply attached to or detached from any type of chair, wherever the user goes. Real-time alerts and visualizations are convenient, user-friendly, and most importantly very effective in aiding a user in adjusting his or her sitting postures, and in discouraging unhealthy sedentary behaviors. The availability of historical data over days, weeks, or months to track trends and monitor progress is helpful in improving the user's posture over the long term and preventing undesirable health issues arising from sitting for extended periods of time. In addition, minimal configuration may be necessary as automatic profiling of the user's body type may be performed via a calibration process. Some embodiments of the present invention provide social and gamification elements such as the ability to poke friends, collecting points for rewards, setting long-term posture goals, and winning discounts or coupons based on correct postures. Again, such gamification and social features may make the posture monitoring and correction process more interactive and fun, thus motivate the user to participate more, and improve sitting postures over time.

In some embodiments, the present invention may be further integrated with other healthcare systems. While health sensors may monitor health indicators such as heart rate and stress level for alert generation, such historical data may also be sent to a primary health practitioner to assist with medical examination and diagnosis, for further improvements in the user's overall health and state of wellbeing. In some embodiments, medical predictions and diagnostic assistance based on historical data collected by the smart seat cover system may be provided to the user directly. In response, the user may be made aware of potential issues, and may be encouraged to seek professional medical assistance before easily overlooked symptoms turn into illnesses that require treatments.

"BACKGURU" is a trademark name carrying embodiments of the present invention, and hence, the aforementioned trademark name may be interchangeably used in the specification and drawing to refer to the products/services offered by embodiments of the present invention. The term BACKGURU may also be used in this specification to describe the overall system of the present invention. Nonetheless, BACKGURU is only one possibility, whereas some embodiments of the present invention may have names other than BACKGURU, for example, in different countries, regions, and markets, under different product models or towards different customer bases.

System Architecture

Figure 2:
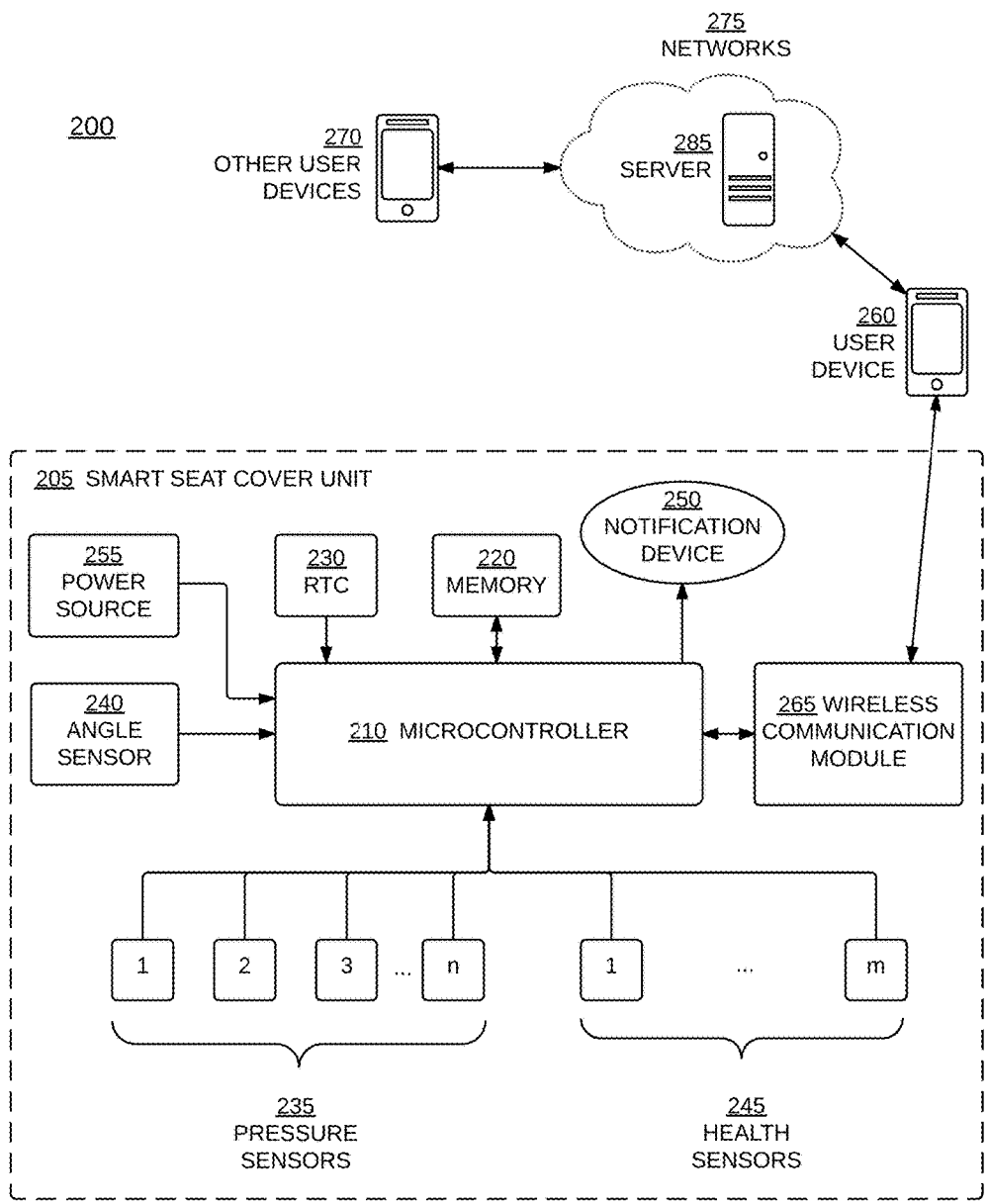
FIG. 2 is an illustrative schematic diagram of the smart seat cover system for monitoring and correcting sitting posture, according to one embodiment of the present invention.
Figure 3A:
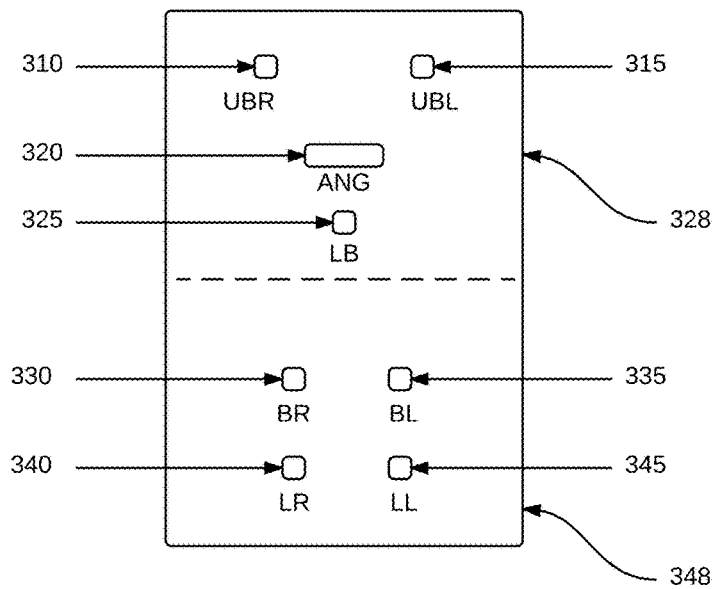
FIG. 3A is an illustrative smart seat cover comprising a backrest portion and a seat portion, according to one embodiment of the invention.
Figure 3B:
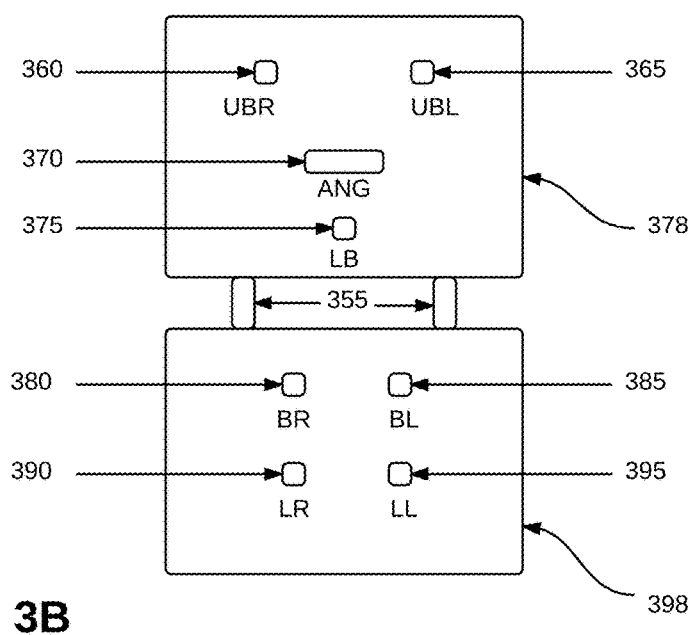
FIG. 3B is another illustrative seat cover comprising a backrest portion and a seat portion, according to one embodiment of the invention.

FIG. 1, FIG. 2, FIG. 3A, and FIG. 3B are schematic diagrams illustrating various components of a BACKGURU smart seat cover system, according to some embodiments of the present invention. In particular, FIG. 1 shows exemplary hardware components of a BACKGURU smart seat cover system fitted to a chair, according to one embodiment of the present invention. FIG. 2 shows a schematic of interconnected electronic components that may enable the operation of the system shown in FIG. 1. FIG. 3A and FIG. 3B are two illustrative designs of portable seat covers with embedded sensors for accurate posture detection, according to some embodiments of the present invention.

More specifically, FIG. 1 shows an illustrative schematic 100 of a sitting posture monitoring and correcting system, also referred to as a smart seat cover system hereafter. The smart seat cover system may comprise a portable smart seat cover 110 with embedded pressure sensors 130 and an angle sensor 150, and optionally a user device 120, shown as a mobile phone in FIG. 1 for illustrative purposes only. In this embodiment, portable smart seat cover 110 may be adapted for attachment to an office chair 160, possibly through some attachment means not shown explicitly in the figure. As previously defined, a seat generally refers to a place, surface, area, or structure designed for an individual to sit on and to support the individual in a sitting position. Exemplary types of seats include, but are not limited to, chairs, stools, benches, car seats, sofas, couches, folding seats, ottomans, and many other structures suitable for sitting. A chair generally refers to a seat with a back, back support, or backrest portion. In the present disclosure, a "seat portion" refers to the part of a chair, sofa, or the like, on which an individual may sit. A "seat portion" may also refer to the part of a seat cover on which an individual may sit. A "seat cover" refers to a cover that may not only attach to a seat portion, but also a back support or backrest portion of a chair, sofa, or the like. A seat cover may encase an entire seat or chair, upper surfaces of a chair, or cover only parts of the seat portion and/or the backrest portion. A seat cover may also comprise paddings to improve user comfort. Attachment means may be in any appropriate form, for example, as front and back straps, elastic fasteners, or Velcro hook-and-loop fasteners secured at appropriate positions. A seat cover may be tailored into fitted chair casings that easily secure to a fitted chair. As the name implies, portable smart seat cover 110 is portable and may be easily transferred from one place to another, wherever the user desires. In some embodiments, portable smart seat cover 110 may come in several sizes for a user to choose from based on his or her height and weight, and for maximizing the accuracy of the posture identification process disclosed herein. When a user is seated in chair 160 equipped with portable smart seat cover 110, pressure sensors 130 and angle sensor 150 measure values that are processed for posture identification, as shall be explained in more detail with reference to FIG. 2. While a smart seat cover system may be a stand-alone device, in some embodiments, the smart seat cover system may further comprise an optional user device, or communicate directly with a user device. A user device such as mobile phone 120 may host a software application for displaying real-time posture visualizations, instructions for posture corrections, historical data, and social or gamification interfaces. In addition, portable smart seat cover 110 and user device 120 may generate alerts when the user has been sitting with an incorrect posture beyond a certain time period, or when the user has simply been sitting for too long. Although shown as a mobile phone in FIG. 1, a user device or end-user device generally refer to a computer with a display, input options, a processor, and a memory, often in the form of a laptop, desktop, tablet, smartphone, wearable devices such as a watch or smart glass, or the like. In some embodiments, a user device may be integrated with other health-monitoring devices and systems.

FIG. 2 shows a schematic 200 of interconnected electronic components that enable the operation of a BACKGURU smart seat cover system. In this embodiment, the smart seat cover system comprises a portable smart seat cover or smart seat cover unit 205 with one or more of the following embedded or attached parts: a microcontroller 210 with a memory 220, a real-time clock (RTC) 230, a total of n pressure sensors 235, at least one angle sensor 240, a total of m health sensors 245, a notification device 250, and a power source 255. Pressure sensors 235, angle sensor 240, and health sensors 245 may be connected to the microcontroller directly or indirectly, with wired or wireless links. In some embodiments, the sensors may be connected to the microcontroller through parallel connections; in some embodiments, the sensors may be connected to the microcontroller through serial connections; in some embodiments, some sensors may serve as relay nodes; in yet some other embodiments, the network configuration within smart seat cover unit 205 may be implemented using an Inter-Integrated Circuit (I2C), multi-master, multi-slave, packet switched protocol which allows multiple devices to share the same buses or communication lines. For example, I2C may use a serial clock line (SCL) and a bidirectional serial data line (SDA) for transmitting information back and forth between masters and slaves within the network configuration shown in FIG. 2. In some embodiments, a user device 260 may be connected to microcontroller 210 via a wireless communication module 265, and to a remote server or cloud server 285, through a network connection 275. Historical pressure, angle, and health data as measured by the sensors and recorded through microcontroller 210 in memory 220 may be uploaded to server 285. Multiple user devices such as 270 may be connected to server 285 for data access and for building an online user community. In some embodiments, multiple seat cover units may be connected to a single user device 260 under the same or different user log-ins to track activities and posture data across all of the seat cover units. For example, a user may use multiple seat covers placed in multiple locations, or a health practitioner may monitor the sitting behaviors of multiple patients concurrently using the same user device. In the latter case, the health practitioner may alternatively access data uploaded to server 285 instead.

In some embodiments, microcontroller 210 may be a ready-made computer board, or a system-on-a-chip (SoC) containing a complete system consisting of multiple processors, multipliers, caches and interfaces on a single chip. SoCs may be implemented as application-specific integrated circuits (ASIC) or using field-programmable gate arrays (FPGA). Microcontroller 210 may first receive signals from the pressure sensors at discrete intervals, before applying posture identification rules to determine sitting postures or positions. Smart seat cover unit 205 may keep a log of posture data in microcontroller 210 or memory 220 along with timestamps as provided by real time clock 230. In some embodiments, historical data stored in memory 220 may be regularly synced and uploaded to user device 260. Alternatively, memory 220 may be non-volatile, and data syncing or upload may be performed only sparsely or upon request. Data may also be synced to user device 260 when a connection is established between user device 260 and seat cover unit 205, for example, upon the initiation of a dedicated user application located on user device 260. Data synced to user device 260 may be automatically backed up to cloud server 285, and may be viewed via other user devices. In some embodiments, memory 220 may be a read-only memory (ROM), such as an EPROM, an EEPROM, or a FLASH memory. Real time clock 230 may be internal or external to microcontroller 210, and may be implemented using a crystal oscillator or a power line frequency.

In different embodiments, pressure sensors 235 may be implemented as piezoresistive strain gauges, capacitive sensors, or may detect pressure by electromagnetic, piezoelectric, optical, potentiometric, or other means. Angle sensor 240 may be implemented using an accelerometer and/or a gyroscope to obtain a relative angular inclination between a seat portion and a backrest portion of smart seat cover unit 205. Health sensors 245 may comprise known technologies for measuring heart rate, blood pressure, breathing rate, stress level, or any other health indicators. In different embodiments, smart seat cover unit 205 may comprise any number of pressure sensors, angle sensors, and/or health sensors. In other words, n and m may be any non-negative integer. For example, one embodiment of the smart seat cover unit may comprise at least five pressure sensors for measuring pressures around leg, shoulder, and lower back areas, a single angle sensor, and no health sensors. Another embodiment may comprise at least seven pressure sensors and a single angle sensor, where two pressure sensors instead of one are deployed for each leg. Yet other embodiments of the present invention may comprise any number of sensors suitable for identifying a given set of sitting postures, to achieve a desired level of sensitivity and accuracy in posture identification, or to accommodate particular limitations on power or energy consumptions. In addition, not all but a subset of embedded sensors may be selectively activated upon automatic or user configurations. In the present disclosure, "embed," "embedding" or "embedded" is used to describe how sensors may be attached to a seat cover. In some embodiments, embedded sensors may be enveloped or enclosed entirely within the seat cover, and hidden from view. In some embodiments, embedded sensors may be partially enveloped or enclosed by the seat cover, with some visibility to the user. In some other embodiments, embedded sensors may be attached to the seat cover using hook-and-loop fasteners or similar attachment means, and may be repositioned by the user as needed. For example, the user may place sensors at one of several sets of pre-determined locations, according to instructions provided by the BACK-GURU system, and based on his or her body size.

In some embodiments, one or more notification devices 250 connected to microcontroller 210 may comprise electronic or piezoelectric components and circuitry, and/or mechanical components for generating alerts. Such alerts may be used for posture correction notification, stand notification, or other similar notification purposes. Exemplary notification devices include buzzers, strobes, speakers, vibrating devices that may generate pinches, nudges, or simple oscillations, and electric shock generators. For a user who has been "idle", that is, seated for at least a pre-configured duration, one or more notification devices may generate mechanical vibrations, mini-electric shocks, or other similar signals to make the smart seat cover unit uncomfortable or even impossible to sit in. In some embodiments, such notifications may be triggered on user device 260 instead, in the form of audio, vibrational, or visual alerts. The decision to trigger a notification alert may be made by microcontroller 210, or user device 260. In some embodiments, notification device 250 may even be a separate wearable such as a watch or a bracelet connected via a body area or personal area network protocol such as Bluetooth, to receive signals from microcontroller 210 or user device 260, and to generate visual, audio, or vibrational notifications to the user directly. Wireless communication module 265 may be implemented using Wi-Fi, Bluetooth, GSM/GPS, Radio frequency (RF), or other communication and networking protocols and means. In some embodiments, wireless communication module 265 may be absent, and smart seat cover unit 205 may be used without user device 260. On the other hand, network connections 275 from user device 260 to server 285 may be wireless or wired, and may employ technologies and protocols comprising Ethernet technology, Local Area Network (LAN), Wide Area Network (WAN), an optical network, the internet, or the like.

FIG. 3A and FIG. 3B are two illustrative designs of portable seat covers with embedded sensors for accurate posture detection, according to some embodiments of the present invention. FIG. 3A shows a schematic of a smart seat cover 300 having a contiguous structure with a backrest portion 328 and a seat portion 348. In backrest portion 328, three pressure sensors Upper Back Right (UBR) 310, Upper Back Left (UBL) 315, and Lower Back (LB) 325 may capture pressure readings at the upper back right, upper back left, and the lower back locations exerted by the user on backrest portion 328 respectively, for determining whether the user is properly supported on his or her back, and whether the user's spine is properly aligned, instead of hunching or slouching. In some embodiments, more than three pressure sensors may be embedded in the backrest portion. For example, two pressure sensors may be placed at the lower back instead of just one, to capture pressure readings on both left and right lower back areas. In seat portion 348, there may be at least two pressure sensors for detecting pressure exerted by each leg. In the embodiment shown in FIG. 3A, four embedded pressure sensors, Bottom Right (BR) 330, Bottom Left (BL) 335, Leg Right (LR) 340, and Leg Left (LL) 345 may capture pressure readings at the back right, back left, leg right, and leg left locations exerted by the user at the four corners of seat portion 348 respectively, for determining whether the user is seated in a balanced way between front and back, as well as between left and right. Finally, angle sensor (ANG) 320 embedded in backrest portion 328 may measure the angle between backrest portion 328 and seat portion 348, or between backrest portion 328 and a horizontal level, to check whether the user is leaning too far back. In this embodiment, there are seven pressure sensors and one angle sensor for capturing the pressure distribution on a smart seat cover with both a backrest portion 328 and a seat portion 348. In other embodiments, any number of pressure or angle sensors may be present. In some embodiments, the smart seat cover may be a cover pad for a stool, with just a seat portion but no backrest portion. Such a seat cover may be used to determine whether leg placements and pelvic positions are correct, but not whether the user is slouching or hunching. In such an embodiment, only two pressure sensors may be present, all four sensors BR, BL, LR, and LL may be present, or more than four sensors may be present, for more accurate posture detections.

FIG. 3B shows a schematic of a smart seat cover 350 with a backrest portion 378 and a seat portion 398 attached or joined together via one or more connecting straps 355. In backrest portion 378, three pressure sensors UBR 360, UBL 365, and LB 375 may capture pressure readings at the upper back right, upper back left, and the lower back locations exerted by the user on backrest portion 378 respectively, for determining whether the user is properly supported in the back. In seat portion 398, four pressure sensors BR 380, BL 385, LR 390, and LL 395 may capture the pressure at the back right, back left, leg right, and leg left, exerted by the user at the four corners of seat portion 398 respectively. Finally, angle sensor ANG 370 may measure the angle between backrest portion 378 and seat portion 398 to check whether the user is leaning too far back. In some embodiments, connecting straps 355 may enclose connecting wires or buses for sensor data transmission from individual sensors to an attached microcontroller. Such connecting straps may be in the form of fixed straps, flexible, extendable, or retractable straps, fastened edges, Velcro hook-and-loop fasteners, and may be made of fabric, metal or fiber with soft paddings, and may house wirings or other forms of electrical connections as needed.

A smart seat cover may come in several sizes and shapes, which a user may select based on his or her body size and/or personal preferences. The size of a smart seat cover may also be commensurate with seat or chair sizes, for easy attachment using straps, fasteners or similar attachment means. Generally, the size of a smart seat cover depends on both the user's body size and the target chair size, to ensure that sensors are placed around desired locations, to capture pressure readings corresponding to relevant parts of the seat and the user's body.

While not shown explicitly in FIG. 3A or 3B, in some embodiments, microprocessor 210, memory 220, power source 255, and wireless module 265 may be placed inside the smart seat cover and hidden from plain view. In one example, these components may be placed within padding layers in the backrest portion or the seat portion, to avoid causing discomfort to the user. In another example, these components may be encapsulated and encased, and placed towards the back of the chair, away from the user after the smart seat cover is installed, to maximize heat dissipation from the microprocessor while minimizing user discomfort. Power source 255 may be a rechargeable battery pack.

In terms of network configuration among the sensors shown in FIG. 3A or 3B, sensors in backrest portion 328 or 378 may each be connected single-hop to a master network node. Similarly, sensors in seat portion 348 or 398 may be connected single-hop to another master network node. Each master node may then be connected to the microprocessor placed within or attached to the smart seat cover. In the case where the microprocessor is located within the seat or backrest portion of the smart seat cover, the microprocessor may itself serve as the master node within the seat or backrest portion. In another embodiment for which microcontroller 210 is in the seat portion of the smart seat cover, the microcontroller may receive data from sensors in the backrest portion wirelessly via wireless module 265. Thus, a subset of the embedded sensors may communicate with the microcontroller wirelessly, while other embedded sensors may communicate with the microcontroller through wired links enclosed or embedded within the smart seat cover. Alternatively, wireless modules may be employed in each sensor and the entire setup may be fully wireless.

Posture Identification

FIG. 4 through FIG. 10 provide illustrative examples of correct and incorrect sitting postures, and corresponding sensor engagements on a smart seat cover.

Figure 4:
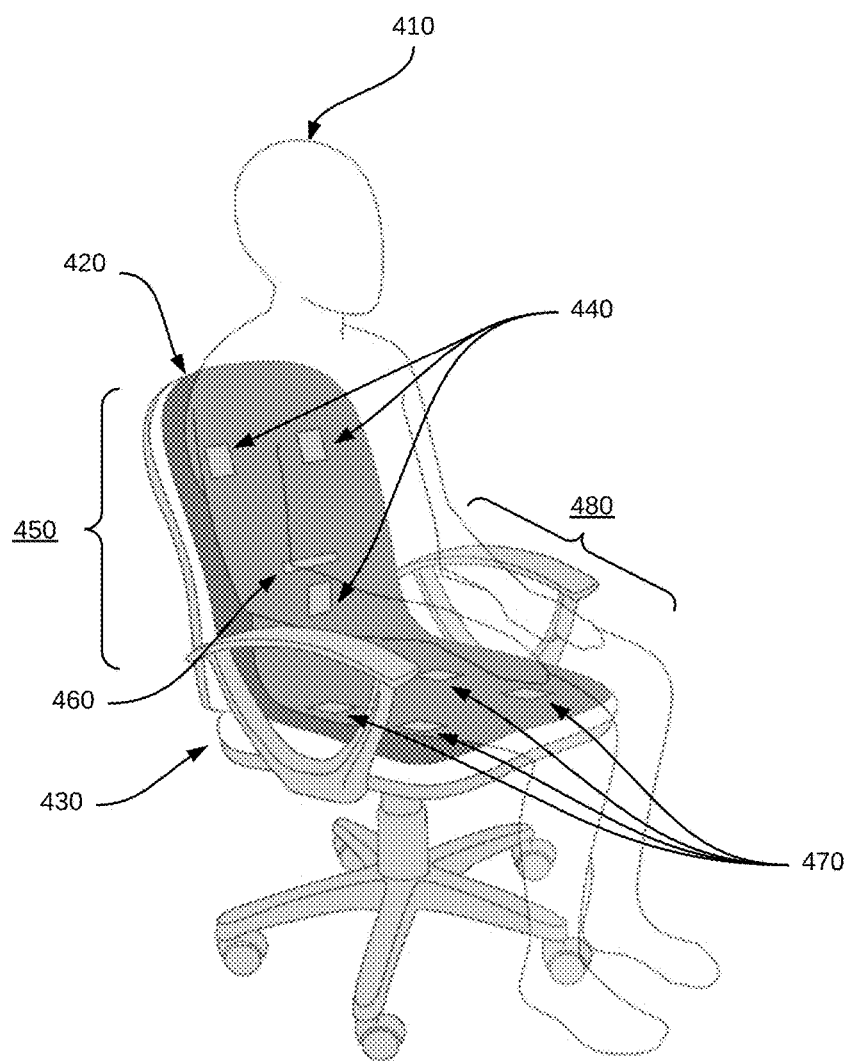
FIG. 4 is an illustrative diagram showing a user seated with a correct posture in a seat equipped with a smart seat cover, according to one embodiment of the present invention.

FIG. 4 is an illustrative diagram 400 showing the avatar of a user 410 seated with a correct posture in a chair 430 equipped with a smart seat cover 420 implemented according to one embodiment of the present invention. Smart seat cover 420 comprises a backrest portion 450 with embedded pressure sensors 440 and an angle sensor 460, and a seat portion 480 with embedded pressure sensors 470. As previously defined, a correct posture refers to an ergonomically acceptable sitting position that keeps the body in alignment to decrease abnormal stress on ligaments and joints, and to allow efficient use of muscles. An ergonomically acceptable sitting position helps prevent strain and overuse of joints, ligaments, bones, and muscles, and helps avoid associated adverse health effects. In the smart seat cover system as disclosed herein, a correct posture may be quantified in terms of acceptable ranges or thresholds for sensor measurement values, and such acceptable ranges or thresholds may be obtained via automated profiling of the user's body type, through a customization or calibration process.

More specifically, In FIG. 4, user 410 is sitting upright in a correct posture, with back straight, shoulders back and relaxed, chest open, hips positioned far back on the chair with lumbar curve supported by the backrest, weight distributed evenly on both hips, and knees leveled with the hips. The user's upper arms also hang naturally close to the body, with the head raised but not tilted forward or sideways. Accordingly, all sensors embedded within smart seat cover 420 are engaged, including pressure sensors 440 and 470, and angle sensor 460. An active sensor may be considered as "engaged" when it reports a non-negligible measurement value. Such a non-negligible measurement value may fall into ergonomically acceptable ranges that define correct sitting postures. For example, as the backrest is reclined at an angle between 100 and 120 degrees, angle sensor 460 is engaged, and reports a non-negligible value that fall into this particular acceptable range. In some embodiments, an active sensor may be considered engaged only when measurement values collectively indicate a balanced state for the sitting posture. For example, in FIG. 4, a BR pressure sensor within the seat portion may be considered engaged only when the BR measurement is on approximately the same scale as the BL measurement, indicating a relatively even weight distribution on the hips.

While correct sitting postures may be defined in terms of ergonomically acceptable ranges for sensor measurements, such ranges may need to be configured or calibrated for different users, based on manual or automatic profiling of the user's body size and weight. A small and petite person is likely to exert less force on the seat portion than someone with a stronger build.

Thus, in some embodiments, a customization, scaling, or calibration process may be performed to determine ranges and thresholds for use in identifying correct and incorrect postures. Such a scaling process may require the user to sit in a correct position or posture, such as shown in FIG. 4, and measurements over a calibration period may be taken by each of the engaged sensors. These measurements may then be used for scaling or normalizing pre-determined ranges or thresholds. Additional scaling factors may also be introduced by the user manually. Scaled or normalized ranges and thresholds may be recorded by microcontroller 210, in memory 220, user device 260, or cloud server 285. The system may then determine correct and/or incorrect sitting postures by comparing sensor measurement values with the scaled ranges or thresholds. This calibration process will be discussed in more detail with reference to FIG. 18.

Figure 5:
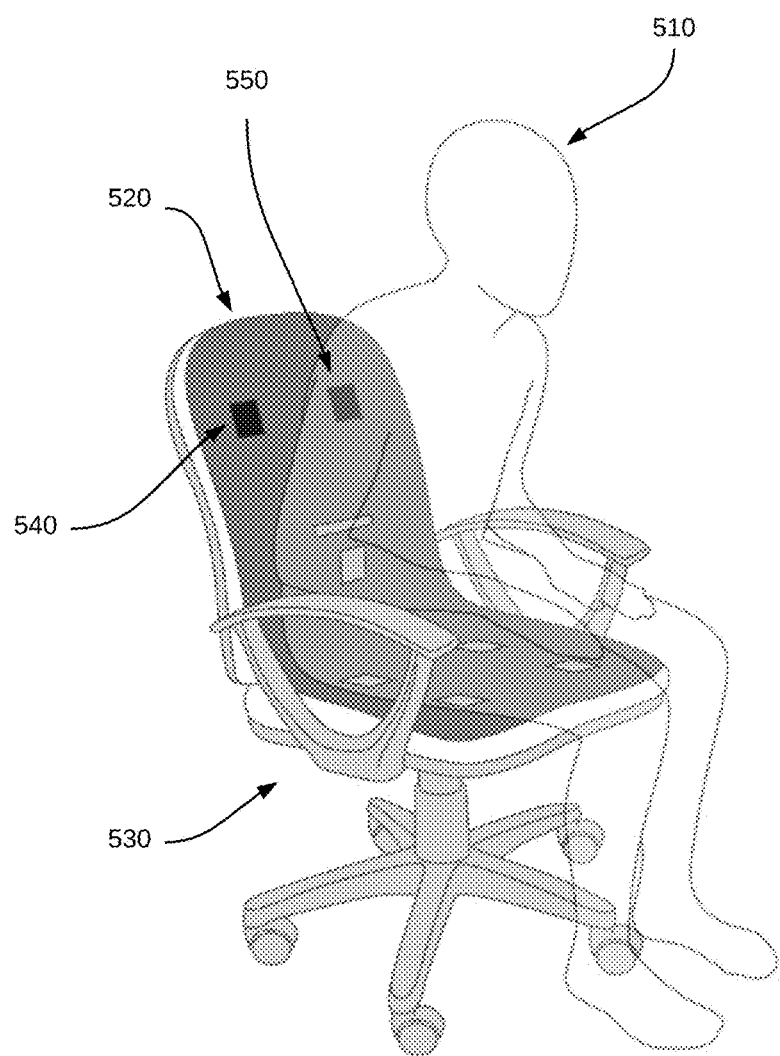
FIG. 5 is an illustrative diagram showing a user seated with a forward leaning posture, in a seat equipped with a smart seat cover, according to one embodiment of the present invention.

FIG. 5 is an illustrative diagram 500 showing a user 510 seated with an incorrect forward leaning posture in a chair 530 equipped with a smart seat cover 520 implemented according to one embodiment of the present invention. Compared with the correct sitting posture shown in FIG. 4, user 510 sits with the upper body leaned forward. Correspondingly, both UBR pressure sensor 540 and UBL pressure sensor 550 may be disengaged, as they may measure negligible or zero pressure readings. Disengaged sensors are shown in a darker shade in FIG. 5. On the other hand, other sensors as indicated in FIG. 5 may be properly engaged to produce non-negligible, valid pressure readings. A forward leaning posture may further comprise specific spine curvatures in the anterior-posterior and/or medial-lateral directions, including shoulder and/or thoracic hunches, unbalanced shoulders, forward bending or arching of the upper and/or lower back, and the like.

Figure 6:
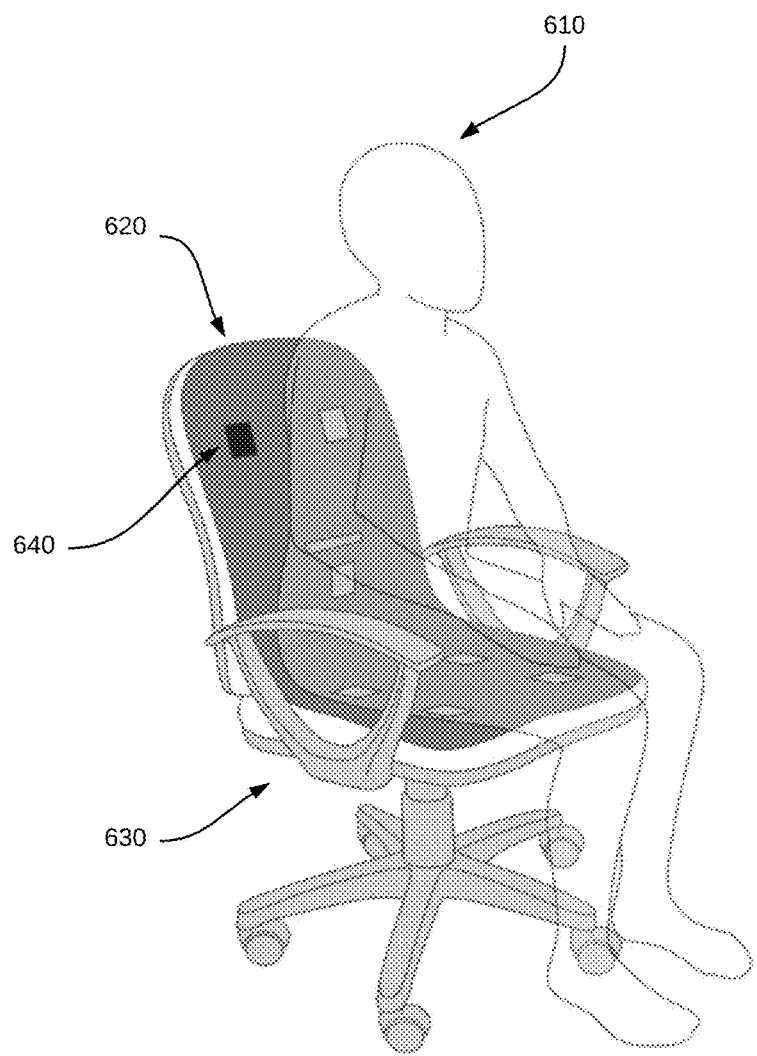
FIG. 6 is an illustrative diagram showing a user seated with a forward leaning posture and unbalanced shoulders, in a seat equipped with a smart seat cover, according to one embodiment of the present invention.

FIG. 6 is an illustrative diagram 600 showing a user 610 seated with another incorrect leaning posture in a chair 630 equipped with a smart seat cover 620 implemented according to one embodiment of the present invention. Compared with the correct sitting posture shown in FIG. 4, user 610 leans forward with unbalanced shoulders, causing UBR sensor 640 to be disengaged. Compared with the forward leaning or hunching posture in FIG. 5 where both shoulders are tilted forward, user 610 is leaning forward in one shoulder and leaning sideways towards the left. As a result, sensor engagement and sensor readings may be different for the two scenarios shown in FIGS. 5 and 6, leading to two different identified postures.

Figure 7:
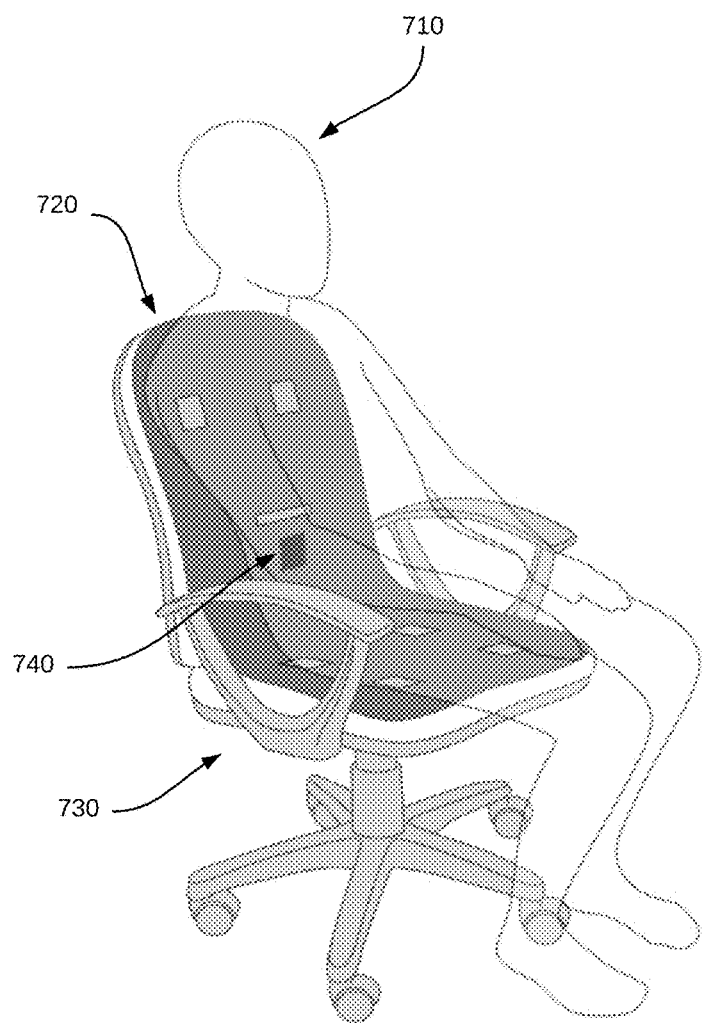
FIG. 7 is an illustrative diagram showing a user seated with an incorrect Lumbar posture, in a seat equipped with a smart seat cover, according to one embodiment of the present invention.

Similarly, FIG. 7 is an illustrative diagram 700 showing a user 710 seated with a backward-leaning, arched back in a chair 730 equipped with a smart seat cover 720 implemented according to one embodiment of the present invention. In this example, LB sensor 740 is disengaged.

Figure 8:
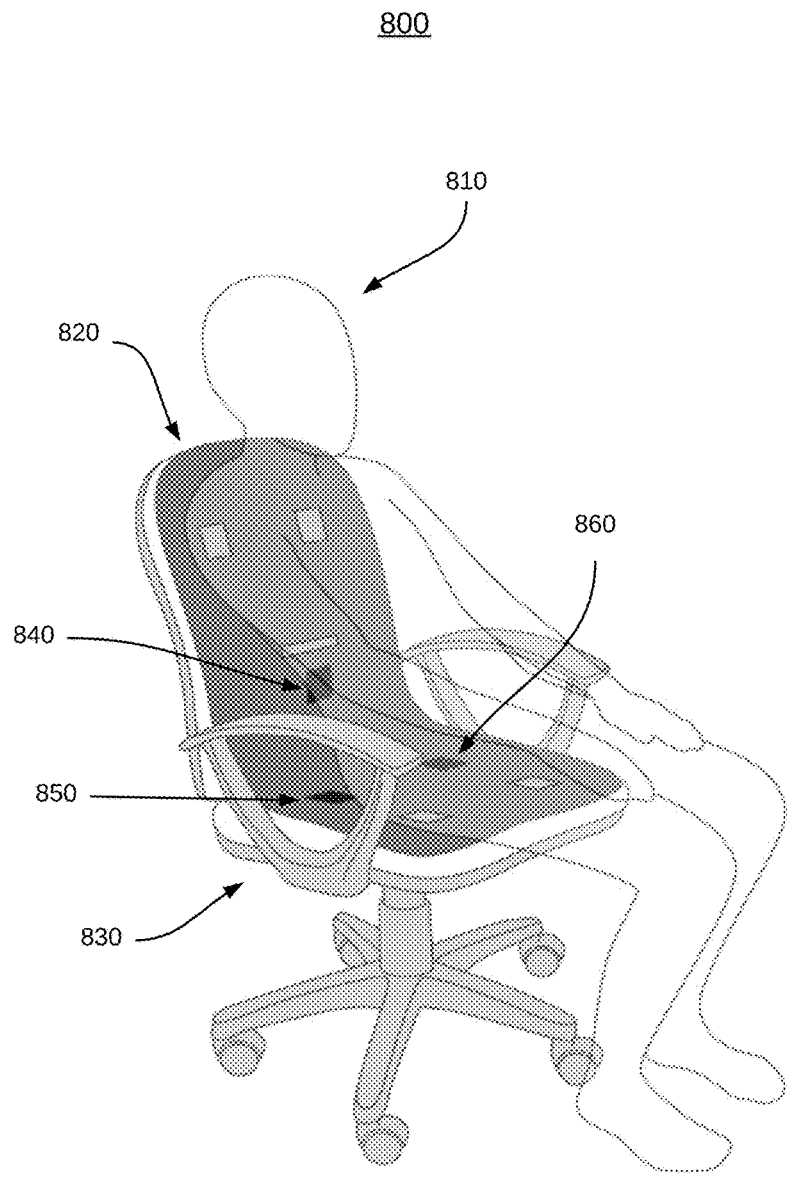
FIG. 8 is an illustrative diagram showing a user seated with a slouching posture, in a seat equipped with a smart seat cover, according to one embodiment of the present invention.

FIG. 8 is an illustrative diagram 800 showing a user 810 seated with a slouching posture in a seat 830 equipped with a smart seat cover 820 implemented according to one embodiment of the present invention. As user 810 droops forward, LB, BR, and BL pressure sensors 840, 850, and 860 become disengaged. Compared with the posture shown in FIG. 7, user 810's upper body leans backwards while his or her hips and legs slide in a forward direction. Sitting with an arched back as shown in FIG. 7 compresses joints in the lower spine and may cause lower back pains. Sitting in a slouched position as shown in FIG. 8 further puts more strain and tension on the neck and shoulder area, and may cause back, shoulder, and neck stiffness or pains. Slouching as illustrated in FIG. 8 has the additional disadvantages of discouraging deep, abdominal breathing, and thus leading to low oxygen levels. Hence, it is important to recognize these two postures separately, and target specifically at each for posture improvement. Embodiments of the present invention achieve these goals by intelligent placement and use of pressure sensors. In FIG. 7, only LB sensor 740 at the lower back is disengaged; in FIG. 8, BR sensor 850 and BL sensor 860 at the back of the seat portion of smart seat cover 820 are also disengaged. As a result, different postures are identified, illustrating how embodiments of the present invention are capable of recognizing subtle differences in sitting postures with high accuracy.

Figure 9:
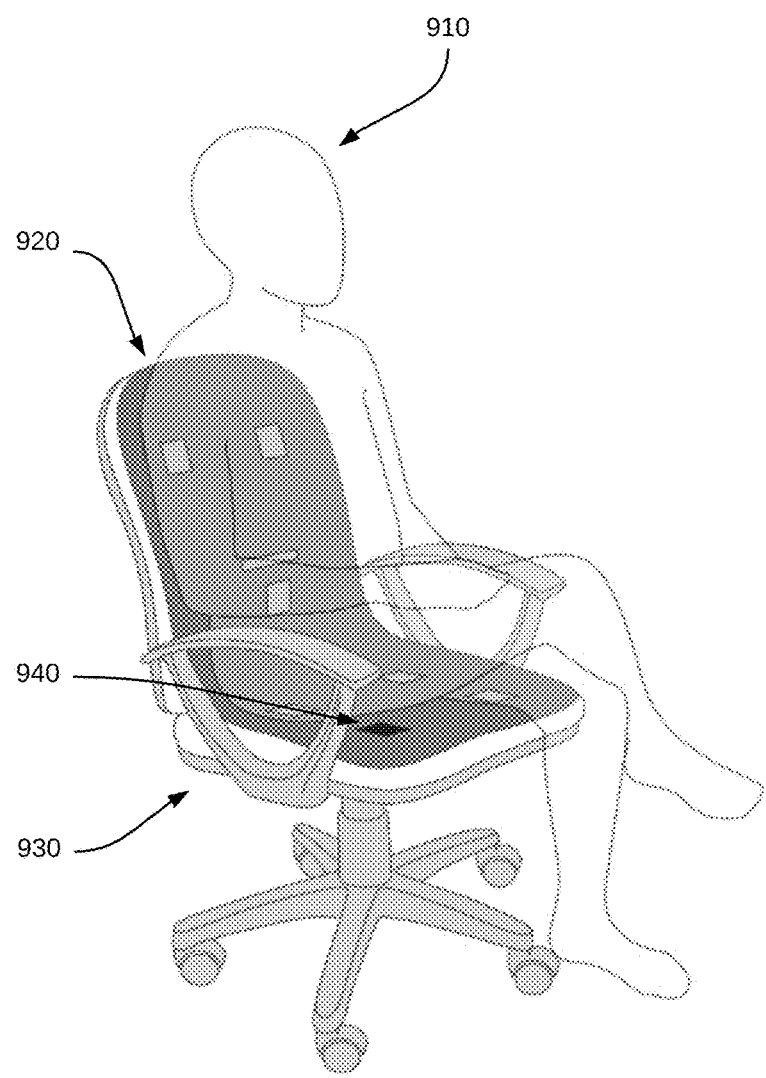
FIG. 9 is an illustrative diagram showing a user seated with a cross-legged posture, in a seat equipped with a smart seat cover, according to one embodiment of the present invention.

FIG. 9 is another illustrative diagram 900 showing a user 910 seated with legs crossed in a seat 930 equipped with a smart seat cover 920 implemented according to one embodiment of the present invention. As the right leg is raised over the left leg, LR sensor 940 is disengaged in this example.

Figure 10:
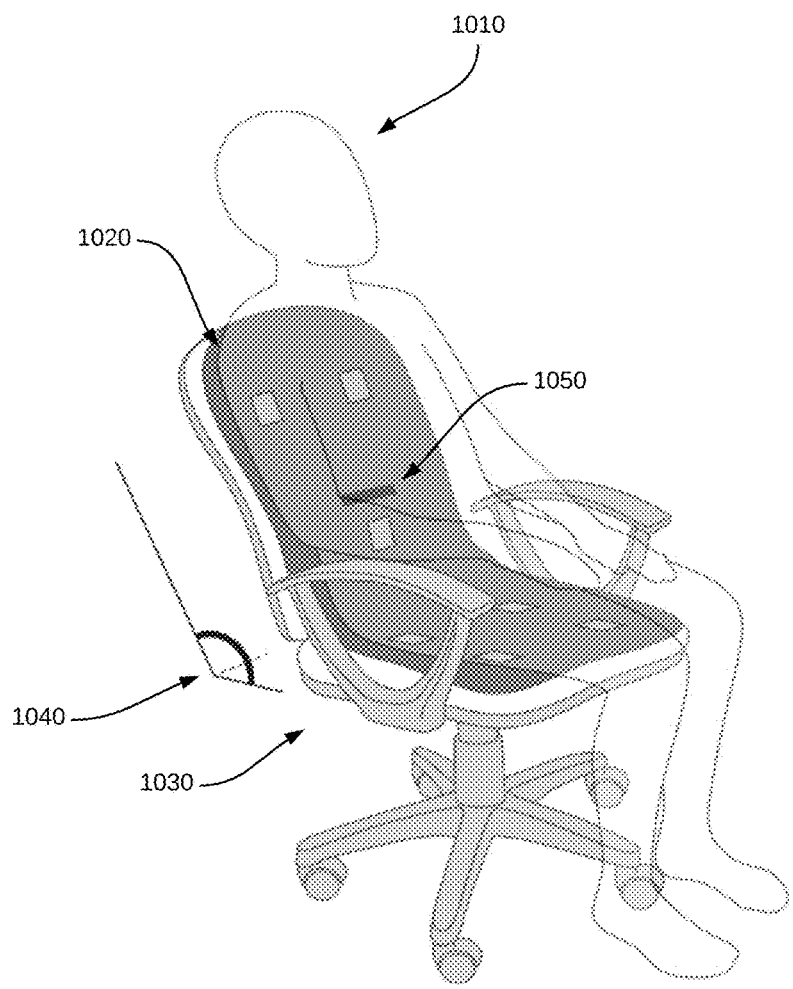
FIG. 10 is an illustrative diagram showing a user seated with an incorrect angle between the legs and the back, in a seat equipped with a smart seat cover, according to one embodiment of the present invention.

FIG. 10 is yet another illustrative diagram 1000 showing a user 1010 leaning back in a seat 1030 equipped with a smart seat cover 1020 implemented according to one embodiment of the present invention. The back-leaning may be detected by angle sensor 1050, which may measure an angular value 1040 that falls outside an acceptable range. For example, if an acceptable range is between 100 and 120 degrees, an angular measurement of 140 degrees signals a back-leaning posture. In this example, angle sensor 1050 has been colored with a darker shade to illustrate the abnormalities in its measurements. Other sensors as shown are engaged and may measure acceptable pressure values. This posture in FIG. 10 may seem reminiscent of the incorrect slouching posture shown in FIG. 8 or the back-arching posture in FIG. 7. However, in this example, all pressure sensors are engaged and produces acceptable measurement values, indicating that the user's back, hips, and legs are all well supported. Nonetheless, having too large an angle between the backrest portion and the seat portions indicates that the user may need to crane his or her neck to be able to see in a forward direction. This comparison across the various examples again illustrates how embodiments of the present invention can detect subtle differences between postures with high accuracy, and provide highly effective recommendations for posture improvements.

In different embodiments, depending on user configuration and/or sensitivity settings, the number and types of identifiable incorrect postures may be different. For example, the user may select coarse or fine distinctions between different postures. A coarse setting may lump the postures in FIG. 8 and FIG. 10 under "slouching", where recommendations may be made to the user to sit back and straighten his or her back. A fine setting may differentiate among these examples and other incorrect postures. Such a fine setting may be useful for a user very serious about precise posture improvements, or a medical practitioner wishing to analyze detailed posture behaviors of his or her patients.

Posture Correction and Idleness Alert Generation

FIG. 11 through FIG. 16 are flowcharts and figures illustrating processes for posture correction and idleness alert generation, according to some embodiments of the present invention.

Figure 11:
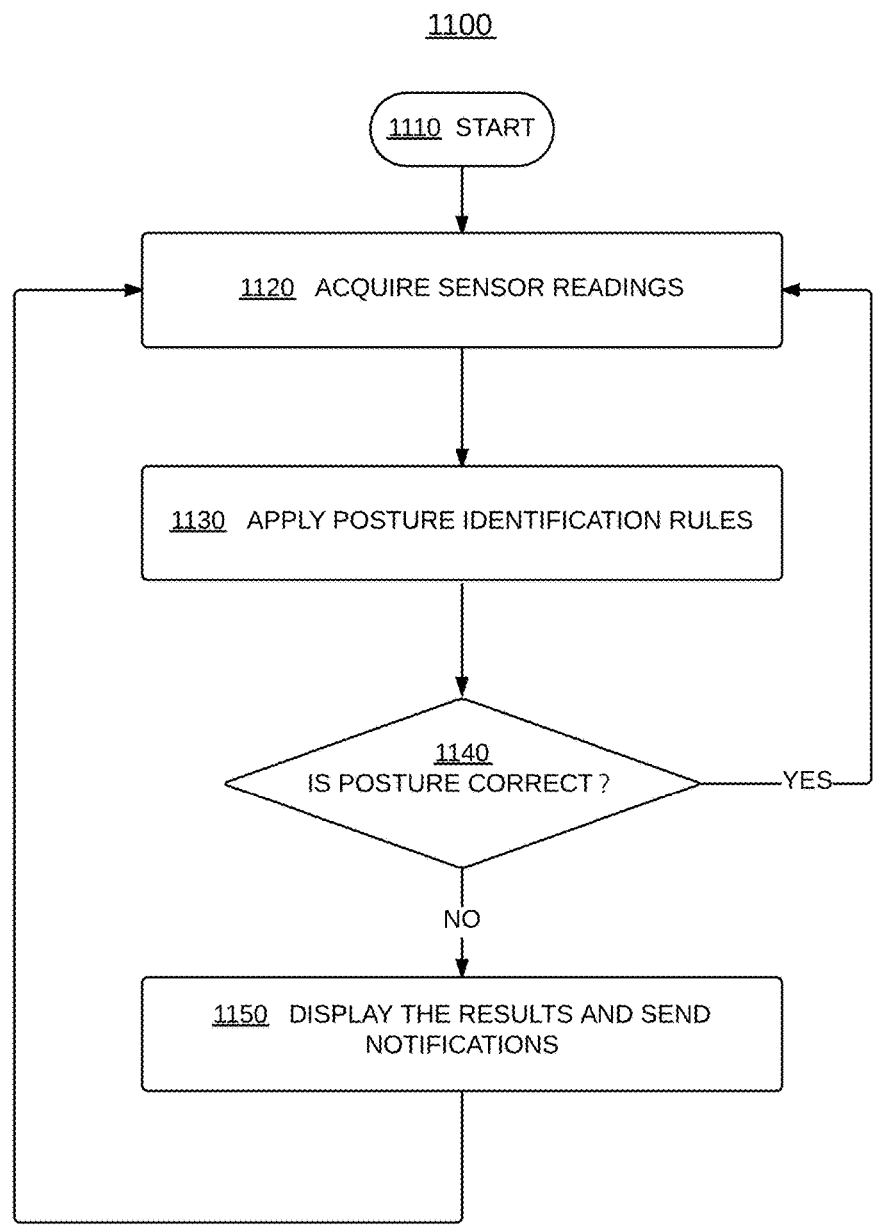
FIG. 11 is a flowchart showing a posture identification process, according to one embodiment of the present invention.

More specifically, FIG. 11 is a flowchart 1100 showing an exemplary posture identification process carried out by a smart seat cover system, according to one embodiment of the present invention. Upon starting at step 1110, sensor readings may be acquired through pressure, angle, and health sensors under the control of a microcontroller at step 1120. Posture identification rules may then be applied on the sensors readings at step 1130. After a posture is identified, it may be checked for correctness at step 1140. If the identified posture is correct, the overall process may return to step 1120 to continue sensor reading acquisition. Otherwise, posture identification results may be displayed and notifications may be generated and sent to a notification device on the smart seat cover system, or to a user device connected with the smart seat cover system. To display the posture identification results, in some embodiments, a real-time visualization of the user's current sitting position may be provided through the user device to aid the user in adjusting his or her sitting position to a correct one. The process continues by looping back to step 1120 to continue sensor data acquisition.

In some embodiments, the sensor reading data acquisition step 1120 as illustrated in FIG. 11 may occur at discrete instances in time, as a continuous process. In other words, data may be constantly acquired while other steps occur in parallel. In addition, data acquisition rate or sampling rate may be automatically determined by the smart seat cover system or manually configured by the user. For example, in the case where sample rate is automatically determined, sensor readings may be acquired every second or every 5 seconds when the microcontroller is fully charged, but every 2 minutes or even 5 minutes when any of battery, memory, or processing capacity is low. Alternatively, the user may set a high sampling rate to keep vigilant about the correct posture, or a low sampling rate to reduce the number of alerts or interruptions. In addition, a higher sampling rate may be necessary if the user shakes his or her legs as a habit and the system has been configured to detect such "oscillations" in pressure readings. Moreover, the smart seat cover system may intelligently learn the user's posture behavior and adjust sampling rate accordingly. For example, the smart seat cover system may alternate among multiple sampling rates, going from every 5 seconds, to every 30 seconds, or every minute, to identify body movements or shifts that may only be detected at particular sampling rates, and use such information in posture identification and/or in warning the user about undesirable posture behaviors. In case of a leg-shaking user, the system may even decrease the sampling rate in general to more accurately detect this behavior.

FIG. 12 is a table 1200 illustrating one exemplary set of posture identification rules, according to one embodiment of the present invention. These rules, listed in the second column of the table, may classify a user's sitting position into one of 37 postures listed in the first column of the table, based on pressure and angle sensor measurements. For illustrative purposes, threshold values or range boundaries are parameterized and represented by variables X1 through X100. Such thresholds and ranges may be determined during the calibration process upon a first use of the smart seat cover system. In this particular example, posture 1 to 36 are incorrect, and posture 37 refers to a correct sitting posture. In other words, sensor measurement values that do not fall into any of the first 36 postures may be considered a correct posture. Some of these incorrect postures may be broadly categorized. For example, forward leaning or hunching as in posture 1, back arching as in posture 4, slouching as in posture 5, shoulder leaning as in postures 2 and 3, unbalanced weight distribution as in postures 6 and 7, leg crossing as in postures 8 and 9, and wrong angle between the upper and lower bodies as in posture number 10.

In this exemplary set of posture identification rules, postures 1 through 10 are "one-error" postures. For example, in posture 1, the UBR and UBL sensors in the upper back both have very low pressure values, corresponding to the incorrect hunching position in FIG. 5. In postures 8 and 9, one leg is crossed over the other, and the difference between the LR and LL pressure values exceeds certain given thresholds. On the other hand, postures 11 through 36 are "combined-error" postures, each containing several one-errors corresponding to the first ten incorrect postures. For example, posture 25 is a combination of posture 1 and posture 8, where the user is crossing over his or her right leg over the left, while hunching at the same time. Thus, a posture identification rule corresponding to a "combined-error" posture may be viewed as a combination or an intersection of simple rules each corresponding to a "one-error" posture. Similarly, any set of multiple individual rules as listed in FIG. 12 may be viewed as a combined posture identification rule. In the present disclosure, "a posture identification rule" may refer to a simple rule, a combined rule, or any unions, combinations, or intersections of sets of simple rules.

In some embodiments, posture identification rules as listed in FIG. 12 may be applied in a sequential order. That is, the posture identification algorithm may check each and every rule listed, starting from the first. Alternatively, the posture identification algorithm may check the first ten rules only, to determined which one or which ones are met, and if necessary, map the result to corresponding "combined-error" postures 11 to 36. Other decision trees are also possible. If none of the first 36 rules are met, the smart seat cover system may identify the user's posture as correct posture 37.

While parameterized in FIG. 12, pressure sensor measurement values and threshold values may have any unit appropriate for the type of pressure sensor deployed. For example, pressure readings may be in terms of voltages (mV), resistance (ohms), conductance (micro-mhos), or force (Newton, N). Assuming arbitrary measurement units, some exemplary sensor measurement values for a correct posture may be UBR=344, UBL=350, LB=254, BL=620, BR=594, LR=723, LL=740. On the other hand, given a UBR reading of 45 and a UBL reading of 46, with thresholds X1=X2=200, it may be inferred from rule 1 that the user is hunching in incorrect posture 1. If a LR reading is 63 and a LL reading is 649, then LL-LR is greater than X10=200, indicating that the user is sitting with imbalanced legs, with the right leg crossed over, corresponding to incorrect posture 8. Another set of exemplary values are UBR=80, UBL=55, LR=70, LL=719, for which both rule 1 and rule 8 are satisfied for X60=X61=X62=200, and the user may be inferred to be sitting in incorrect posture 25.

Figure 13:
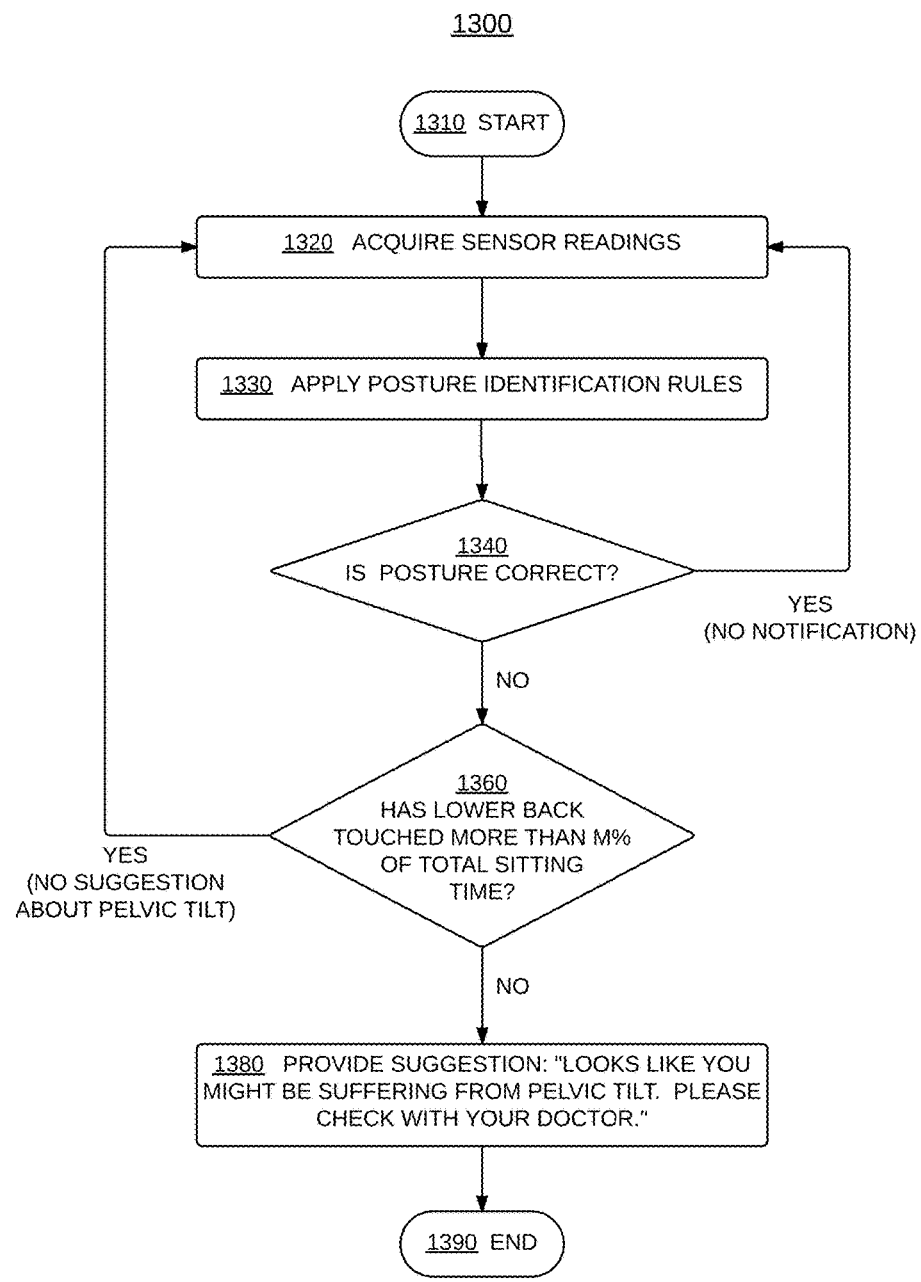
FIG. 13 is a flowchart showing a pelvic tilt detection process, according to one embodiment of the present invention.

FIG. 13 is a flowchart 1300 showing a pelvic tilt detection process, according to one embodiment of the present invention. This process goes one step beyond merely detecting postures at any given instant to inferring a possible medical condition. Pelvic tilt refers to the orientation of the pelvis with respect to the thighbones and the rest of the body. Pelvic tilt may take on several forms, including anterior, posterior, and lateral, respectively referring to having the pelvis tilting towards the front, the back, or either side of the body. Embodiments of the present invention is able to detect anterior pelvic tilt with lumbar extension. When a person with this condition sits down, his or her lumbar spine curves forward, making it highly likely that no contact would be made with the lower back sensors embedded in the smart seat cover. If all other parts of the body are positioned correctly and applying pressure to all sensors other than the lower back sensor, that is, when all sensors have acceptable values except LB sensor 325 or 375, then a "lower back not touched" error may be triggered, corresponding to posture 4 in FIG. 12. If a user regularly sits in this fashion, triggering this specific error in isolation and not in combination with other errors, it may be suspected that the user could suffer from anterior pelvic tilt. For such users, the smart seat cover system may suggest a physical examination by a medical practitioner for this specific condition.

To perform the pelvic tilt detection process, the smart seat cover system may first obtain sensor readings at step 1320, after process initiation at step 1310. Posture identification rules may be applied at step 1330 and the identified posture checked for correctness at step 1340. If the posture is correct, the system may issue no notification and loop back to obtain sensor readings at step 1320 again. Otherwise, the system may check, at step 1360, whether the user is in posture 5, a one-error posture where the lower back has touched the smart seat cover and exerted non-negligible pressure on the LB sensor, for more than a predefined percentage M % of a total sitting time. Upon determining that this is the case, the smart seat cover system may make no suggestions about pelvic tilt and loop back to step 1320. However, if it is determined at step 1360 that the lower back has not touched the smart seat cover for more than M % of the total sitting time, a possible pelvic tilt has been detected, and a suggestion may be made to the user to see a doctor at step 1380. The process may be terminated at step 1390. Early detection of pelvic tilt before any symptoms are exhibited may be very useful in preventing further worsening of the condition.

Figure 14:
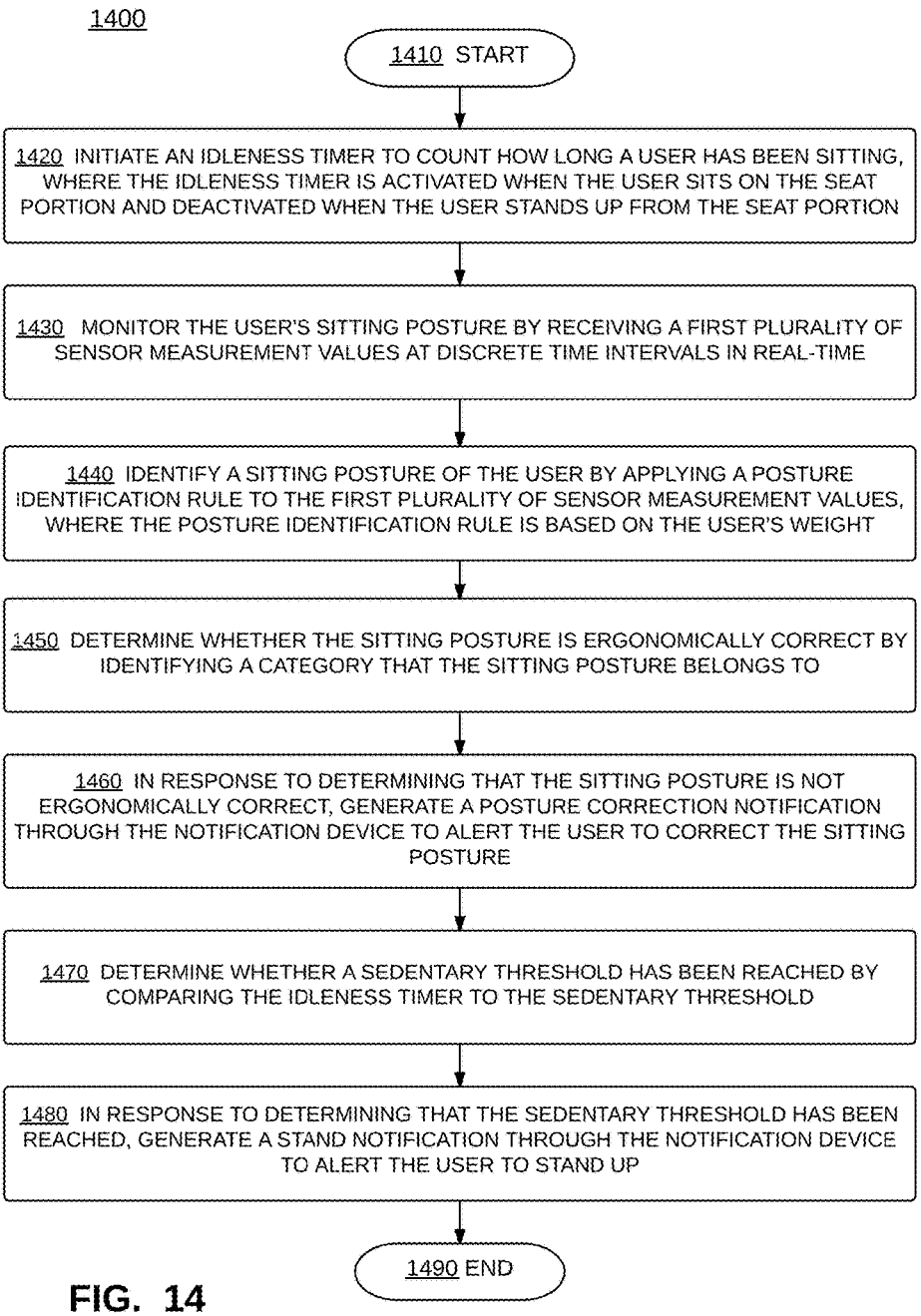
FIG. 14 is a flowchart showing a process for monitoring and correcting sitting posture of a user, and for discouraging sedentary behavior of the user, according to one embodiment of the present invention.

FIG. 14 is a flowchart 1400 illustrating a process for monitoring and correcting sitting posture of a user, and for discouraging sedentary behavior of the user, according to one embodiment of the present invention. Upon starting at step 1410, the system initiates an idleness timer at step 1420 to count how long the user has been sitting, where the idleness timer is activated when the user sits on the seat portion of a smart seat cover, and deactivated when the user stands up from sitting on the seat portion of the smart seat cover. Next, the user's sitting posture is monitored at step 1430, by receiving a first plurality of sensor measurement values at discrete time intervals in real-time. The system may then identify a sitting posture of the user at step 1440 by applying a posture identification rule to the first plurality of sensor measurement values, where the posture identification rule is based on the user's weight, and determine whether the sitting posture is ergonomically correct at step 1450 by identifying a category that the sitting posture belongs to. In response to determining that the sitting posture is not ergonomically correct at step 1460, the system may generate a posture correction notification through the notification device to alert the user to correct the sitting posture. At step 1470, the system may determine whether a sedentary threshold has been reached by comparing the idleness timer to the sedentary threshold; and in response to determining that the sedentary threshold has been reached, a stand notification may be generated at step 1480 through the notification device to alert the user to stand up, before the process ends at step 1490. In some embodiments, additional optional steps may be inserted, for example, in allowing a delay between detecting an incorrect sitting position and sending the notification based on a pre-configured time duration set by the user. In addition, the sedentary threshold may be configured by the user to be any number of minutes, such as 1 minute or 30 minutes.

Figure 15:
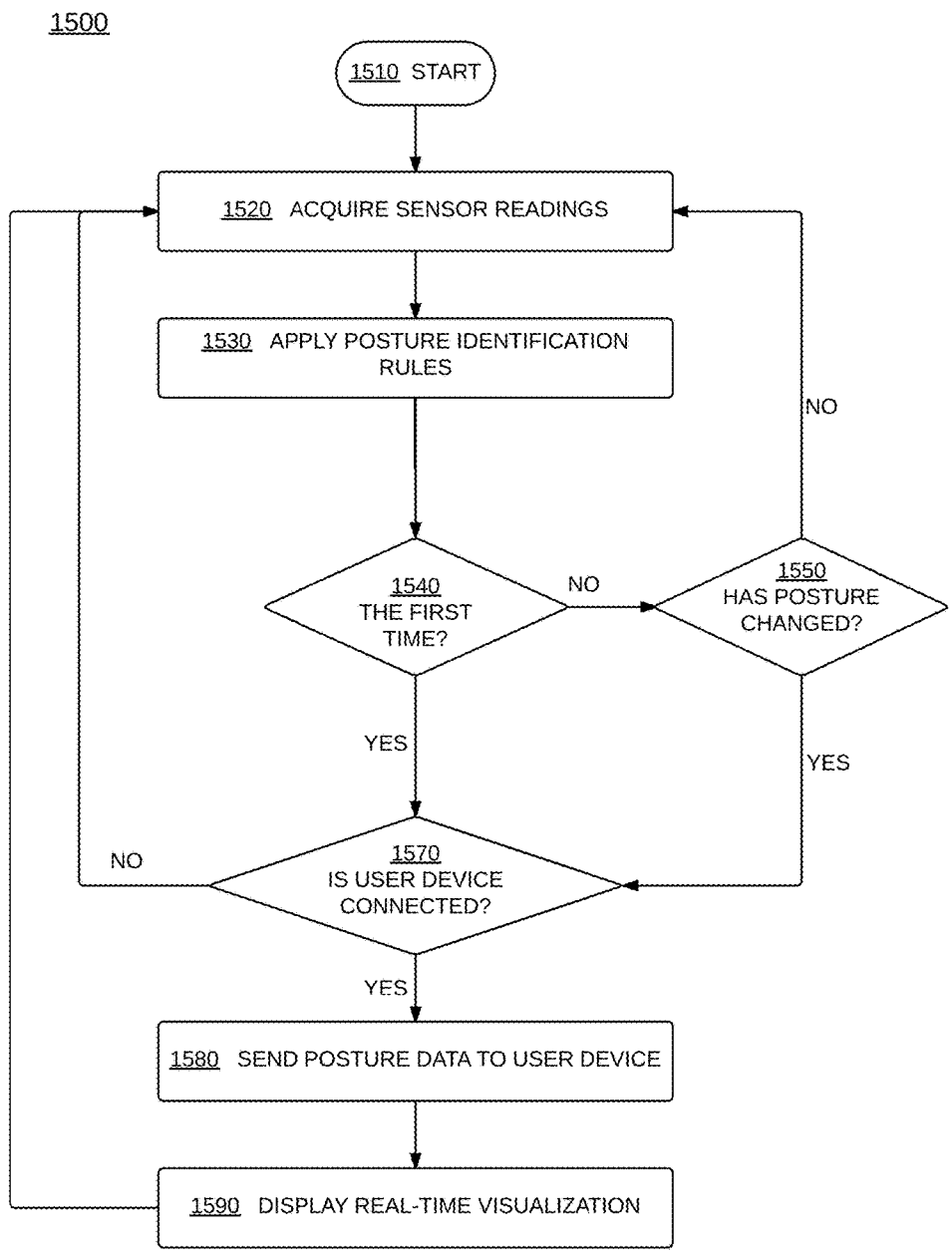
FIG. 15 is a flowchart showing steps of a real-time visualization and notification process, according to one embodiment of the present invention.

FIG. 15 is a flowchart 1500 showing steps of a real-time visualization and notification or alert process for aiding the user in adjusting his or her position into the correct one, according to one embodiment of the present invention. In short, given a set of sensor measurements and an identified posture, the identified posture may be displayed visually in real-time on a user device interconnected with the smart seat cover. As more measurements are collected, such a real-time visualization may only need to be updated when a change in posture is detected. More specifically, upon starting at step 1510, sensor measurement values may be acquired at step 1520, and posture identification rules may be applied at step 1530. If the system determines at step 1540 that it is the first time the system has performed posture identification, the overall process continues to step 1570 to determine whether user device 120 is connected. If the posture identification step 1530 has previously been performed and a "prior posture" is being displayed on the user device, the system may determine at step 1550 whether a posture change has occurred, by comparing the prior posture and the current posture, or by comparing current sensor measurement values to stored prior sensor measurement values. In response to determining that a posture change has not occurred, the system may continue to display the prior posture on the user device. However, if a posture change has occurred, the overall process may continue to step 1570 to check whether the user device is connected. If the user device is connected, the processor may send posture data to the user device at step 1580, and prompts the user device to display a real-time visualization of the updated posture at step 1590. In some embodiments, vibrational feedback, wireless alerts, and other forms of notifications may also be generated at step 1590, in addition to or in place of the real-time visualization data, based on the sensor measurement and posture data.

Figure 16:
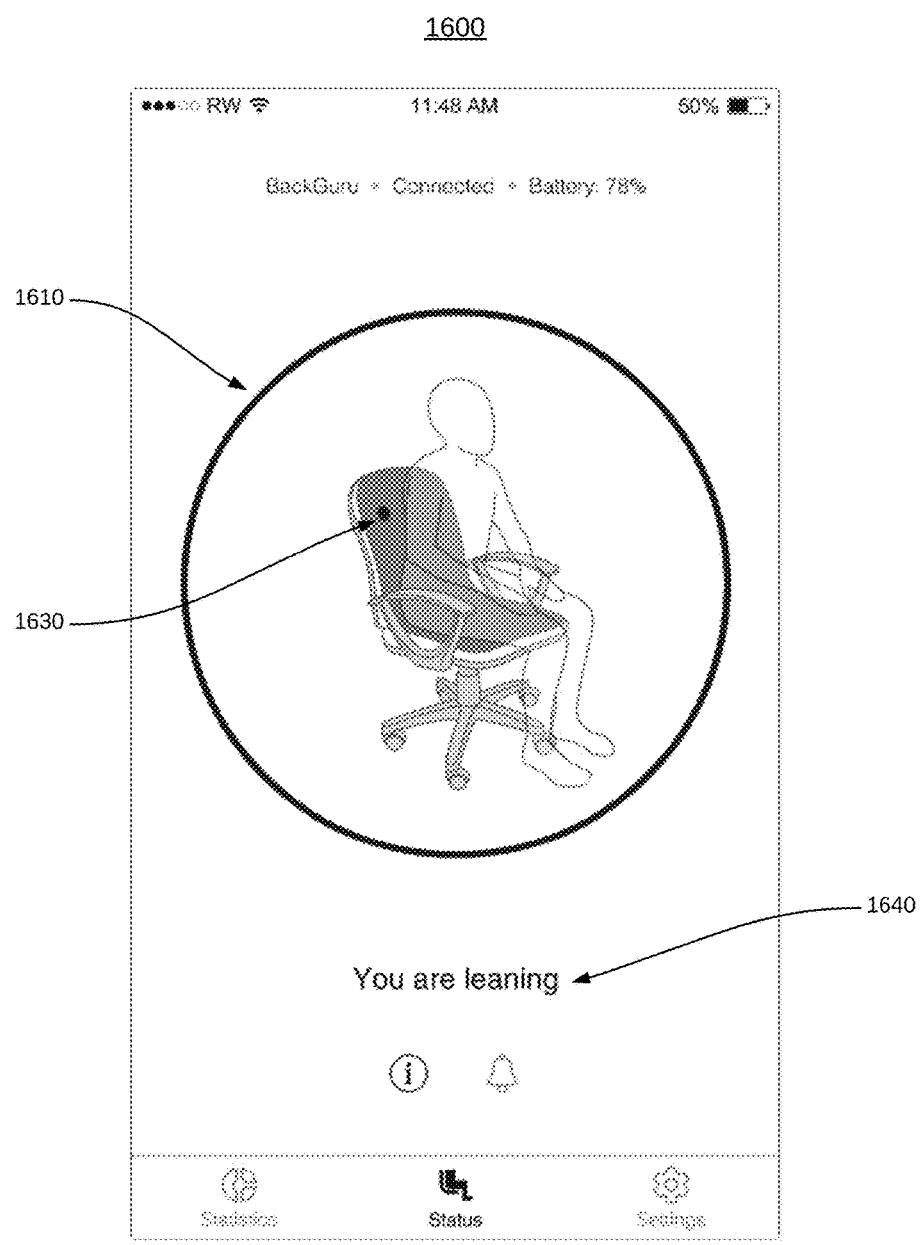
FIG. 16 is one example of real-time visualization via a user device, according to one embodiment of the present invention.

FIG. 16 is an illustrative diagram 1600 of an exemplary real-time visualization 1610 via a software application installed on a user device, according to one embodiment of the present invention. Such a visualization may be generated by the user device upon receipt of data or control signals from the smart seat cover, in step 1590 of the process shown in FIG. 15. Based on data sent to the user device at step 1580, the current sitting position is shown with UBR sensor 1630 highlighted or shaded to indicate disengagement of the sensor. An error text 1640 "You are leaning," "You are leaning forward," "You are leaning left," "You are hunching," "You are slouching," "You are arching your back", or "You are leaning back too far" may also be shown to indicate the type of incorrect position the user is in. Visualization 1610 and error text 1640 provide real-time feedback in helping the user understand what changes in posture may be needed. In some embodiments, the user may choose to turn off such visual or textual notifications in a "do not disturb"

mode. In some embodiments, the user may also individually configure notification devices on the smart seat cover system.

Figure 17:
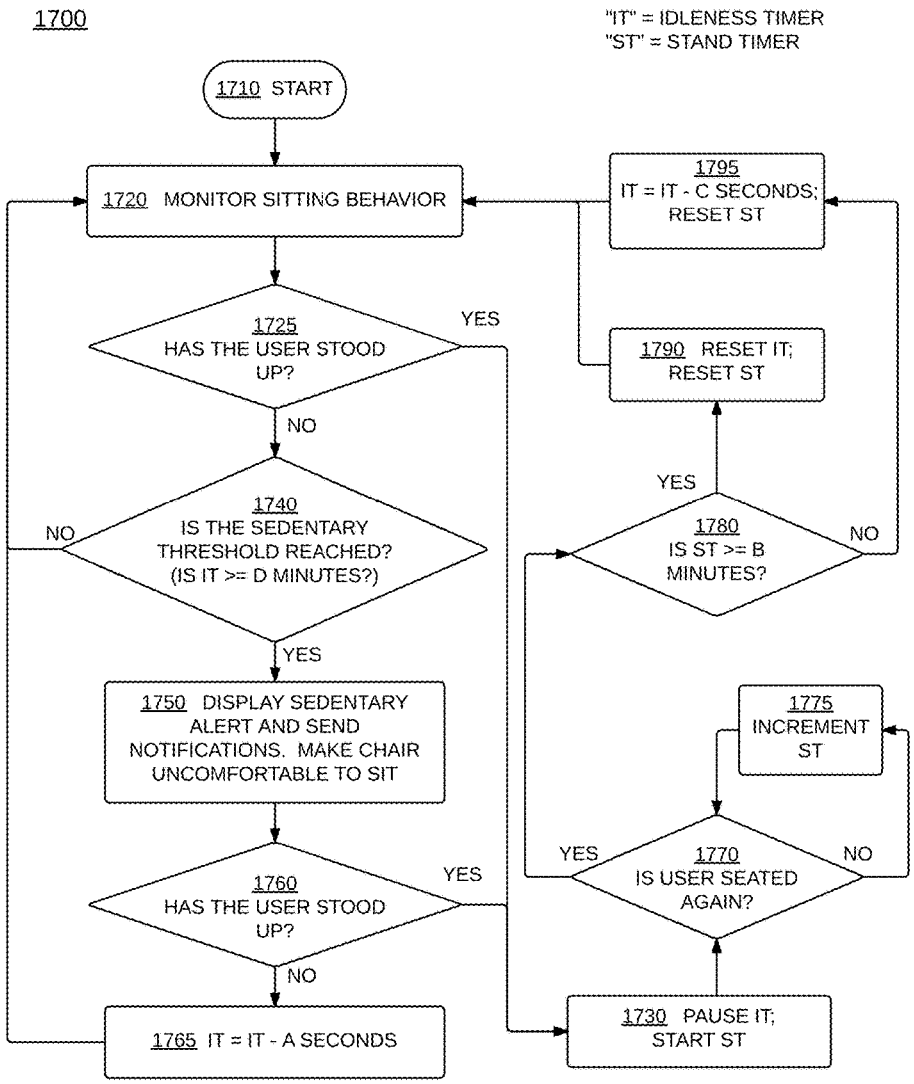
FIG. 17 is a flowchart showing an idleness identification process, according to one embodiment of the present invention.

FIG. 17 is a flowchart 1700 showing an idleness identification process for discouraging sedentary behaviour, according to one embodiment of the present invention. The goal of this process is to ensure that, when the user has been sitting for a period of time that exceeds a sedentary threshold, he or she would be alerted to stand up and take a motion break. In addition, upon detecting that the user has been sitting or been idle for at least a predetermined period of time, the notification device may make the seat uncomfortable or even impossible to sit on via an electric shock or some other means, such that the user is compelled to get up and walk around or stretch, instead of continuing to be idle.

More specifically, in one embodiment of the present invention, the smart seat cover system may initiate a stand timer (ST) to count how long the user has been standing, where the stand timer may be activated when the user stands up from sitting on the seat portion of the seat cover, and deactivated when the user sits on the seat portion of the seat cover. Similarly, the smart seat cover system may initiate an idleness timer (IT) to count how long the user has been idle, where the idleness timer may be activated when the user sits on the seat portion of the seat cover, and deactivated when the user stands up from sitting on the seat portion of the seat cover.

Upon starting at step 1710, the BACKGURU smart seat cover system may monitor sitting behaviour at step 1720 and determine whether the user has stood up at step 1725. In response to determining that the user has stood up, the idleness timer may be paused at step 1730 until the user is seated again, while the stand timer may be activated, and incremented at step 1775 until it is determined that the user has seated again at step 1770. In response to determining that the user has not stood up at step 1725, the smart seat cover system may determine whether the sedentary threshold is reached at step 1740. If the sedentary threshold has not been reached, the system may loop back to step 1720 to monitor the user's sitting behaviour. If at step 1740 it is determined that a sedentary threshold of D minutes has been reached, the system may send a stand notification to the user by making the chair uncomfortable to sit on via a notification device and/or by displaying a sedentary alert via a user device at step 1750. After a very short delay, the system may determine whether the user has stood up in response to the stand notification at step 1760. If the user has not stood up in response to the stand notification, the system may reduce the idleness timer by a predetermined idleness grace period of A seconds at step 1765, then loop back to step 1720 to monitor the user's sitting behaviour. By decrementing the idleness timer at step 1765, the user may be given a snooze period of A more seconds before the stand notification is sent again.

If it is determined at step 1760 that the user has stood up in response to the stand notification, the system may pause the idleness timer until the user is seated again and activate the stand timer at step 1730. The system may then determine whether the user is seated again at step 1770. If it is determined that the user is not seated again, the stand timer may be incremented at step 1775, and the incrementation process continues until the user is seated. Once the user is seated, the system may determine whether a standing time threshold of B minutes has been reached at step 1780. In response to determining that the standing time threshold has been reached, the system may reset both the idleness timer and the stand timer at step 1790, before returning to monitor sitting behavior at step 1720; in response to determining that the standing time threshold has not been reached, the system may reduce the idleness timer by a predetermined idleness grace period of C seconds, and reset the stand timer at step 1795, before returning to monitor sitting behavior at step 1720. As time progresses, the user may reach the sedentary threshold again in C seconds, and receive a stand notification at step 1750. The requirement for not sitting down for at least B continuous minutes may now be fulfilled, since the stand timer had been reset at step 1795. The standing time threshold, B, as well as the idleness grace periods A and C, may be configured by the user, for example, to be any number of seconds or minutes between some thresholds such as 1 and 30.

The following example illustrates how this process for discouraging sedentary behavior may work. Assume a user has been sitting for 30 minutes, which is the sedentary threshold. The idleness timer records a sitting time of 30 minutes, and the notification device makes the chair uncomfortable to sit on by administering mini-electric shocks at step 1750. Assume the user does not stand up, and the system reduces the idleness timer by a grace period of A=60 seconds at step 1765, while continuing to monitor sitting behavior at step 1720. Thus, the idleness timer is updated to 29 minutes and continues to run. 60 seconds later, the sedentary threshold is reached again at step 1740, and the user is again alerted to stand up at step 1750. Assume the user stands up this time around, and the idleness timer is paused, while the stand timer is started. Until the user sits down again, the stand timer continues to be incremented at step 1775 by the time elapsed. Next assume the standing time threshold is B=10 minutes, but the user is seated again after only 90 seconds, so at step 1780, it is determined that the user has not stood up for long enough, and stand timer is reset at step 1795, such that the next time the user stands up from sitting, they would have to stand for the entire duration of the standing time threshold B of 10 minutes. However, at 1795, the idleness timer may also be reduced by a grace period of C=120 seconds, leading to an idealness timer count of 28 minutes. In 120 seconds from this point on, the sedentary threshold is again reached at step 1740, and the user is again asked to stand up at step 1760. The idleness timer may only be reset when the user has stood up for the entire period of the standing time threshold B after which the stand timer is reset. The presence of the grace periods A and C allow for flexibility in case the user is very busy at work, yet also allowing the user to get a short stretching break. The configurable sedentary threshold and standing time threshold also allow for flexibility, since the standing time threshold can be as short as one minute, which may still provide the great benefit of a water break and remind the user to reset and get into a correct posture when seated again.

Calibration

Figure 18:
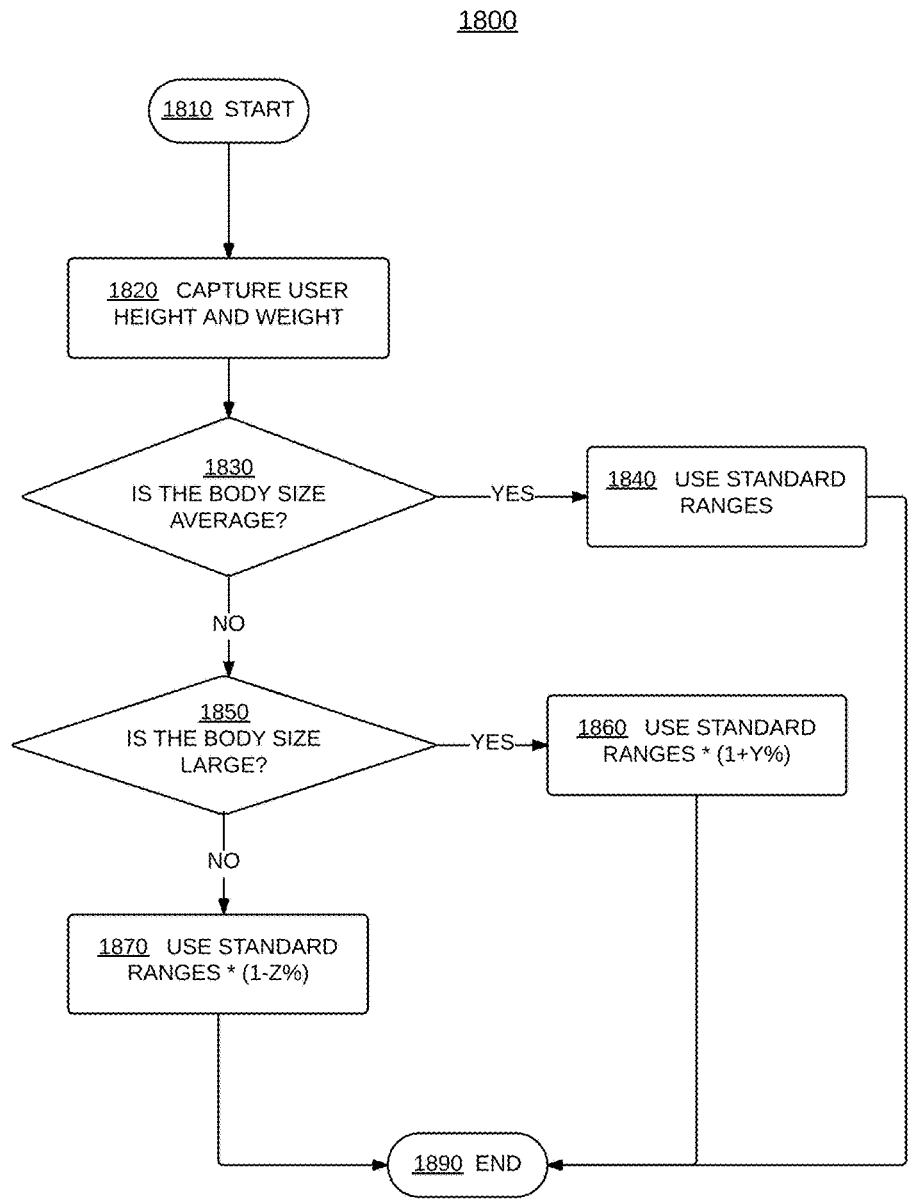
FIG. 18 is a flowchart showing the process of body type identification for automated profiling of a user's body type, according to one embodiment of the present invention.

FIG. 18 is a flowchart 1800 showing the process of body type identification and automated profiling of a user's body type for scaling thresholds or ranges for posture identification, according to one embodiment of the present invention. This calibration process may be performed during a first time use of the smart seat cover system, periodically, or upon user request. In some embodiments, the process may be performed whenever the system detects a significant change in the user's condition, for example, more than 10% change in user body weight as indicated by uniformly increased or decreased pressure sensor readings.

In this embodiment, a user's body type may be classified into three types: small, medium, and large. Upon the start of the process at step 1810, the system may receive height and weight information of the user at step 1820, for example, via user input, and may then determine whether the user's body size is average at step 1830. If the answer is yes, standard ranges of thresholds for pressure values may be used at step 1840. If the answer is no, the system may check if the body size is large at step 1850. If this second check is affirmative, the standard ranges may be expanded by Y % at step 1860. Otherwise the body size is determined to be small, and the ranges for thresholds may be reduced by Z % at step 1870. In some embodiments, there may be a different number of body types than three. For example, some people may have large hip sizes or broader shoulders than average, and the corresponding pressure distributions across the sensors may be different from someone whose upper and lower bodies have more even weight distribution. In the case of someone with larger hips but average build otherwise, it may be more accurate to use a larger range for the thresholds in the seat portion of the smart seat cover, and the standard ranges for the backrest portion.

In some embodiments, the user may be required to input his or her height and weight before the system performs an automatic profiling process to assign acceptable pressure thresholds and ranges for identifying ideal sitting postures or positions. More specifically, instructions on how to sit correctly may be given through a user interface or client application on a user device to a user seated in a chair equipped with a smart seat cover. Upon opening the client application for the first time, the user may be prompted to input his or her user name, height, weight, and whether he or she has chronic back pain. The system may then provide instructions on how to set up the system by attaching the smart seat cover unit to the chair, on how to switch the BACKGURU smart seat cover unit on, and how to connect it to the user device by enabling a wireless communication link, such as through Bluetooth. A systematic calibration process may then take place, through textual instructions and accompanying visualizations on the user device. For example, the application may instruct the user to push his or her hips as far back as they can go into the chair, by showing an avatar of the user sitting in a chair and with the hips highlighted with arrows pointing towards the back of the chair. The application may also instruct the user to adjust an anterior-posterior tilt of the upper body while slightly leaning on the back rest, to achieve a 100 to 120 degree reclined angle between the backrest and seat portions of the smart seat cover. Such instructions may be interactive, as the client application examines real-time pressure and angle sensor readings to ensure the user's body is upright and balanced in the seated position. In some embodiments, the user may be further reminded to relax his or her shoulders, to adjust or remove the armrests if they are in the way, and to adjust the seat height so that his or her feet are flat on the floor and knees are at the same level or slightly lower than the hips. In some embodiments, the user may be required to maintain a correct posture for a certain calibration period, such as 30 seconds, 60 seconds, or 90 seconds, for the auto-profiling or calibration process to complete. Measurement values from engaged pressure sensors and angle sensor, may be averaged across the calibration period to obtain a calibration reference for scaling ranges and thresholds for posture identification. In some embodiments. users of different body shapes or having different body weight distributions may require further adjustments to the scaled ranges and thresholds. For example, females generally have wider hips and may exert relatively more pressure on the BR and BL pressure sensors.

In embodiments where the BACKGURU system is used alone without a user device, the calibration process may be completed using the steps disclosed above, except real-time feedback may be provided through audio instructions or vibrational notifications instead of real-time visualizations.

In some embodiments, acceptable ranges and thresholds may be determined by adjusting the measured values recorded at the end of the calibration process and expanding these measured values into ranges or thresholds, without reference to any standard ranges. In some embodiments, the height and weight of a user may be treated separately, by providing Short, Medium, and Tall sizes of smart seat covers for selection, and the automated profiling process may have separate ranges for small, medium, and large, or short, medium, and tall individuals. Separate ranges may also exist for males and females, since for individuals with the same height but of different gender, the weight distributions are different.

Personal Diagnostics, Posture and Health Improvements Using Historical Data

Figure 19A:
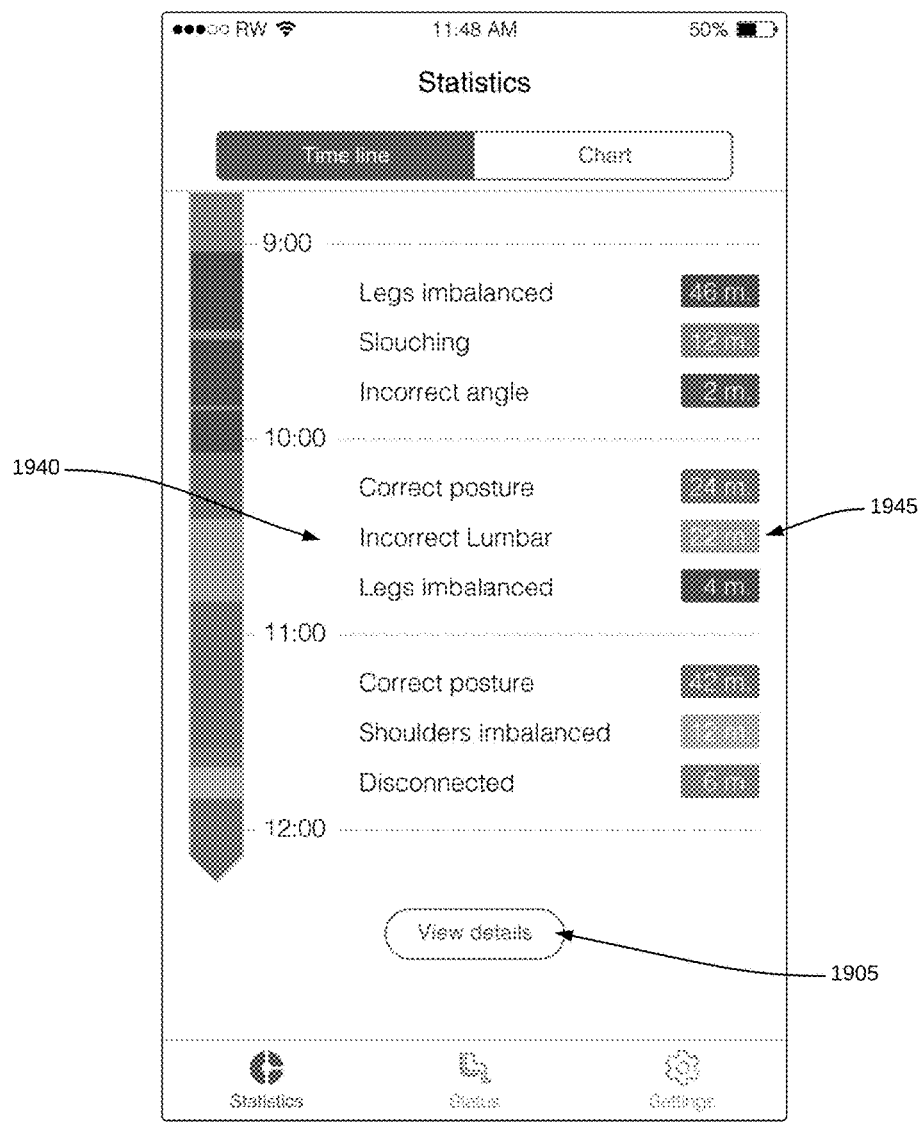
FIG. 19A is an illustrative figure showing a display of user historical data in the form of a timeline, according to one embodiment of the present invention.
Figure 19B:
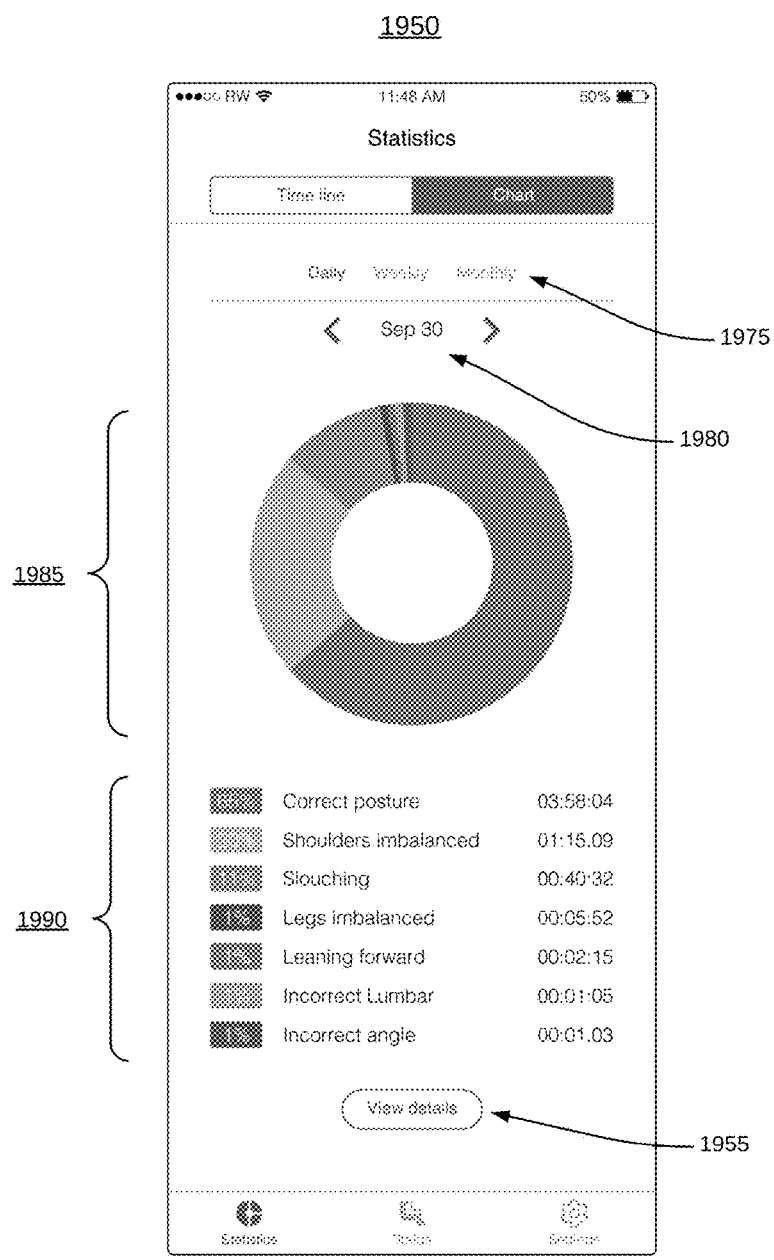
FIG. 19B is an illustrative figure showing a display of user historical posture data in the form of a dashboard, according to one embodiment of the present invention.

The present invention has many features and functionalities aimed at improving personal health. As discussed above, the present invention monitors posture by means of pressure sensors and an angle sensor. Statistics of historical data may be displayed on a user device for the user to keep track of his or her sitting habits and track his or her progress of posture improvement over time. FIG. 19A and FIG. 19B illustrate sample statistics on historical posture data, as displayed via a user device, to assist the user in keeping track of his or her progress in posture improvements.

FIG. 19A is an illustrative screen capture 1900 of a user device showing historical posture data for a user in the form of a timeline, according to one embodiment of the present invention. In this example, different posture statuses such as an incorrect lumbar posture 1940 are displayed along a vertical timeline that has been indexed hourly. Status durations such as 1945 are also displayed in minutes for each posture.

FIG. 19B is another illustrative screen capture 1950 of a user device showing historical posture data in the form of a pie chart, according to one embodiment of the present invention. In this example, posture pie chart 1985 illustrates the relative proportions of time the user has spent in different postures on September 30, as indicated by the highlighted "Daily" option on a duration selection panel 1975 and the date "Sep 30" on a date panel 1980. Similar pie charts may also be generated across weekly or monthly data. Below posture pie chart 1985, a legend 1990 shows the percentages and durations spent in each different posture.

The ability to select between posture timelines and posture pie chart enable the user to review his or her posture statistics on the high level, over a day, a week, a month, or in detail on an hourly-basis. Such historical data and statistics may be shared by the user with friends or their medical practitioners.

Both FIGS. 19A and 19B show a "View details" button 1905 and 1955 at the bottom of the screen. Upon clicking on such a link, the user may be taken to a more complete and detailed page that lists the amount of time spent on each posture during a given time duration, such as the day September 30, the morning of September 30, between any given hours on September 30, or some other day, selected work days, weeks, months, or any other consecutive or non-consecutive time durations that may be chosen from a pop-up calendar. In addition to postures listed in FIG. 19B, other exemplary postures that may be listed on the details page include, but are not limited to, correct posture, wrong angle, leaning forward, right leg imbalanced while learning forward, lower back not touched while leaning forward, right leg imbalanced and lower back not touched while learning forward, too much weight on the right, leaning left, glute not touching and lower back not touched while leaning forward, slouching and lower back not touched. In addition to lists, graphs such as bar charts and scatter plots may also be generated or displayed. In some embodiments, the number or types of postures thus displayed in the details page may be configurable, where the user may select from predetermined posture lists, or select individual postures for summary and display, depending on the user's personal preferences and goals.

Furthermore, depending on sitting movement patterns, the stress level of a person may be detected, by analyzing historical data statistically using machine learning algorithms such as Naïve Bayes and various training datasets. The system may further include health sensors that monitor health indicators such as heart rate, blood pressure, various hormone levels, and behavioural sensors, which may, independently or together with the health sensors, monitor stress levels, among other salient behavioural features. Preliminary medical diagnoses and predictions may also be made. The analysis of historical data may be automatic.

Figure 20:
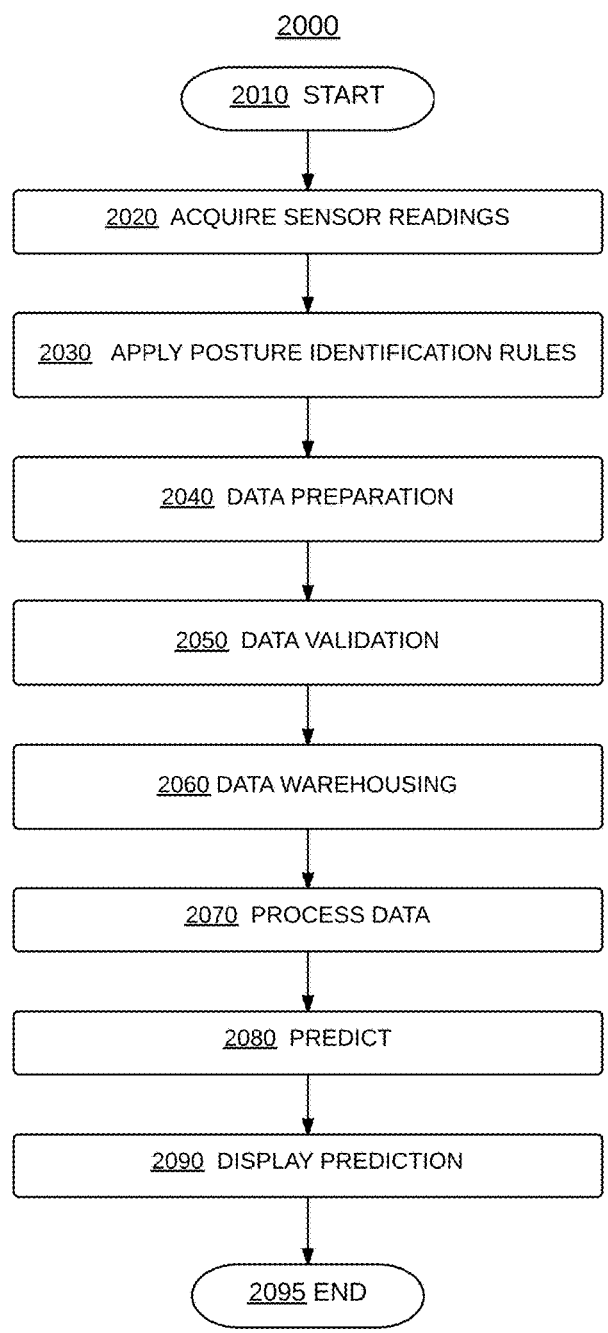
FIG. 20 is a flowchart showing the process of determining medical predictions based on sensor reading history, according to one embodiment of the present invention.

FIG. 20 is a flowchart 2000 showing a process 2000 for determining medical predictions based on sensor reading history, according to one embodiment of the present invention. Upon starting at step 2010, the system acquires sensor readings at step 2020, and applies posture identification rules to these sensor readings at step 2030. The system may then prepare collected posture data and/or other health and behavioural data at step 2040 by properly grouping and formatting the collected data. Data validation may be performed at step 2050 by removing invalid outliners or non-essential data such as correct posture durations. Data warehousing may be performed at step 2060 by reorganizing data into desired data structures. In step 2070, the validated and warehoused data may be processed, for example, using Naïve Bayes classification, K-Means, Support Vector Machine (SVM), a hybrid approach using multiple algorithms, or some other algorithms. Medical predictions may be made at step 2080, and displayed at step 2090 via a user device, before the overall process ends at step 2095. Corrections to postures as necessitated by medical predictions obtained in step 2080 may be presented to the user as personal challenges or suggestions for future improvements. Medical predictions thus obtained may also alert the user on medical conditions that would otherwise be overlooked, and prompt the user to seek proper medical diagnosis and treatments at an early stage.

Figure 21:
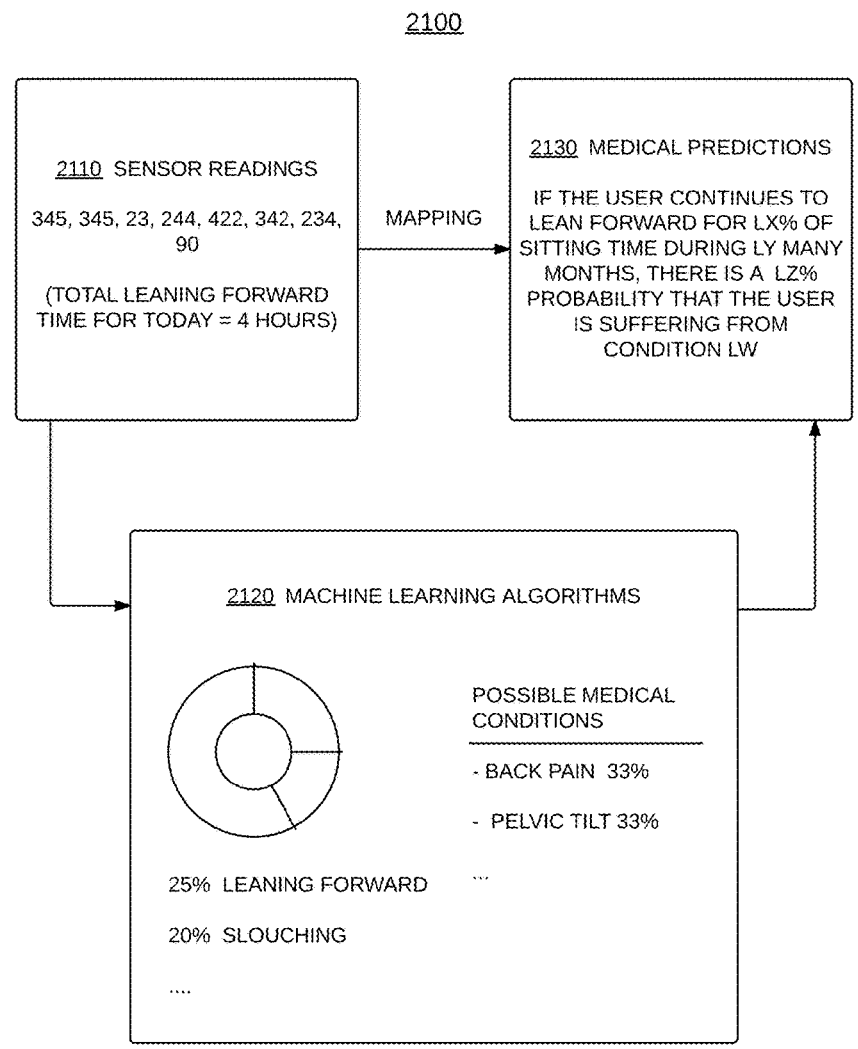
FIG. 21 is an illustrative figure showing an example of mapping historical sensor readings to medical predictions, according to one embodiment of the invention.

FIG. 21 is an illustrative FIG. 2100 showing an example of applying historical sensor readings 2110 to generate medical predictions 2130 according to one embodiment of the present invention. Initial training data may be fed to the system manually by professionals via a web-based admin panel for one or more machine learning or other statistical algorithms 2120, which may be Naïve Bayes classification, K-Means, Support Vector Machine (SVM), a hybrid approach using multiple algorithms, or any other algorithm. Then, current and historical data 2110 from pressure sensor readings, angle sensor readings, health sensor readings, and behavioural sensor readings may be fed to the machine learning algorithms and medical predictions 2130 may be made based on the user's sitting behaviours and/or other health and behavioural data from the sensor readings. For example, a medical prediction may be that "If the user continues to lean forward for LX % of sitting time during LY many months, there is a LZ % probability that user is suffering from condition LW." Medical predictions may be presented to the user via a user device, where the user may be prompted to verify the accuracy of the predictions using Yes/No questions to further refine the predictions. Such user feedback may be used by the algorithms to optimize future predictions and improve their accuracies.

Remote access of current and historical data from these sensors, along with the analysis results, may enable medical practitioners to remotely monitor in real-time the user's sitting patterns and postures, to examine pertinent health indicators such as body weight changes, and to view historical data and statistics. Such medical practitioners may further keep track of body weight changes, manage posture positions and alerts, and remotely change posture setting configurations such as pressure ranges and thresholds for triggering alerts. For example, if a user is prone to forward leaning, his or her medical practitioner may set a more stringent condition for sending an alert by decreasing default thresholds X1 and X2 illustrated in FIG. 12 from 200 to 150, where these values may be measured in any arbitrary or relevant units. This may be achieved by, for example, integrating the system with other medical applications. The above features may help users improve their health over time by heightening their own awareness of their posture habits and other health indicators, and empower their medical practitioners to more effectively and conveniently monitor patient posture and health metrics, and actively engage in the posture improvement of their patients. Similar remote access functionalities may be enabled for other organizations. For example, companies may analyze the sitting postures and behavioral patterns of employees to improve productivity. Embodiments of the present invention may be employed in many other applications and is not limited to medical research and employee behavioral pattern analysis.

Gamification and Social Networking

Some embodiments of the present invention may also provide gamification features to make the posture and sedentary behavior monitoring process more fun, and social features to motivate user participation and interaction. Exemplary gamification and social features include, but are not limited to, personal postural goal setting, personal or group challenges, ranking and community leader boards, winning points or other forms of rewards, and friend circle likes and pokes via networked user devices and notification devices. When a user visits a "Social" menu option in a client software application installed on a user device, he or she may have the ability to connect his or her social media accounts to the application. Once social media accounts are connected, all friends who use the BACKGURU smart seat cover system may be suggested to the user, and each displayed with a "Correct Posture Score" that measures how good one's overall sitting posture is.

There may be different ways of computing a correct posture score. For example, a user may earn P amount of points when he or she has been sitting with a correct posture for a minimum period of time Q. Some postures may worth more than others. In some embodiments, a correct posture score may be linearly related to a correct sitting time, which may be the amount of time for which the user has been sitting correctly. Such a correct posture score may start to be cumulated once the correct sitting time exceeds a given threshold. In some embodiments, longer correct sitting times may weigh more. Thus, proportionally more points may be added non-linearly to the correct posture score for increasing correct sitting times.

In some embodiments, an incorrect posture score may also be computed, where different types of postures may be weighed differently, such that a positive score may indicate that the user hunches more, while a negative score may indicate that the user slouches more.

In some embodiments, users may have the ability to share their posture details with others including friends, employers, medical practitioners, and the like. Once data is shared, the other party may have the ability to view a graphical interface similar to the user's data display. The user may also configure privacy settings to decide which data may be shared with whom. For example, a user may elect to share his or her medical predictions with friends who may also have the same sitting posture issues.

Besides friends' data and posture scores, users may also see Leader Boards among different groups, for example, a Work Leader Board, a Family Leader Board, or a Global Leader Board. A Global Leader Board or group Leader Board may be available with different tiers, such as Gold, Silver, and Bronze, based on users' Correct Posture Scores.

Figure 22:
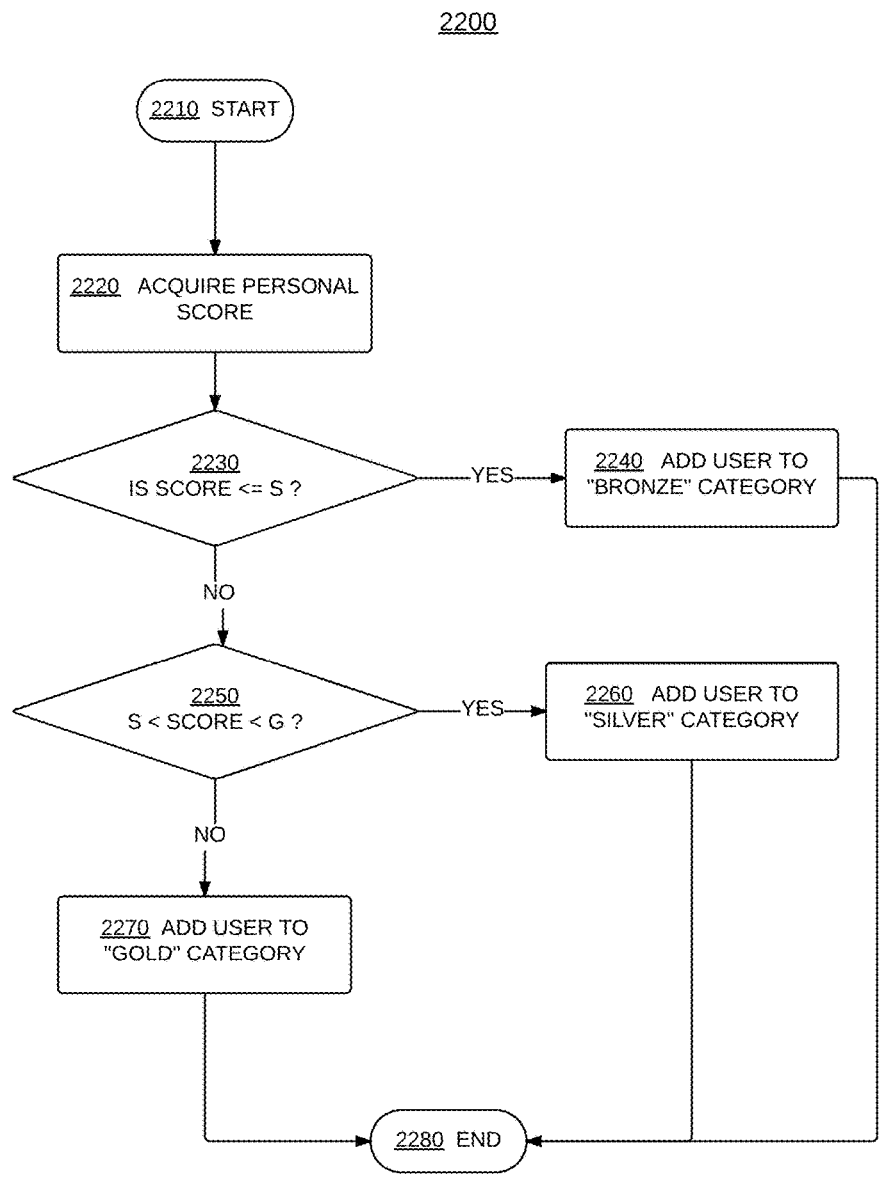
FIG. 22 is a flowchart showing a Leader Board classification process, according to one embodiment of the present invention.

FIG. 22 is a flowchart 2200 showing a Leader Board classification process, according to one embodiment of the present invention. Starting at step 2210, the BACKGURU smart seat cover system may acquire a Correct Posture Score for the user at step 2220, and may determine whether the score is less than or equal to a Silver threshold score S at step 2230. In determining that the score is less than or equal to S, the system may add the user to a "Bronze" category at step 2240, and ends the process at step 2280. In determining that the score is not less than or equal to S at step 2230, the system may further check whether the score is greater than S and less than a Gold threshold score G at step 2250. In determining that the score is greater than S and less than G, the system may add the user to a "Silver" category at step 2260, and ends the process at step 2280. In determining that the score is greater than or equal to G at step 2250, the system may add the user to a "Gold" category at step 2270, and ends the process at step 2280. In other embodiments, there may be other types of rankings or a different number of tiers with different names, and users may earn badges, gold stars, points, discounts, or coupons based on tiers, classifications, and rankings.

Figure 23:
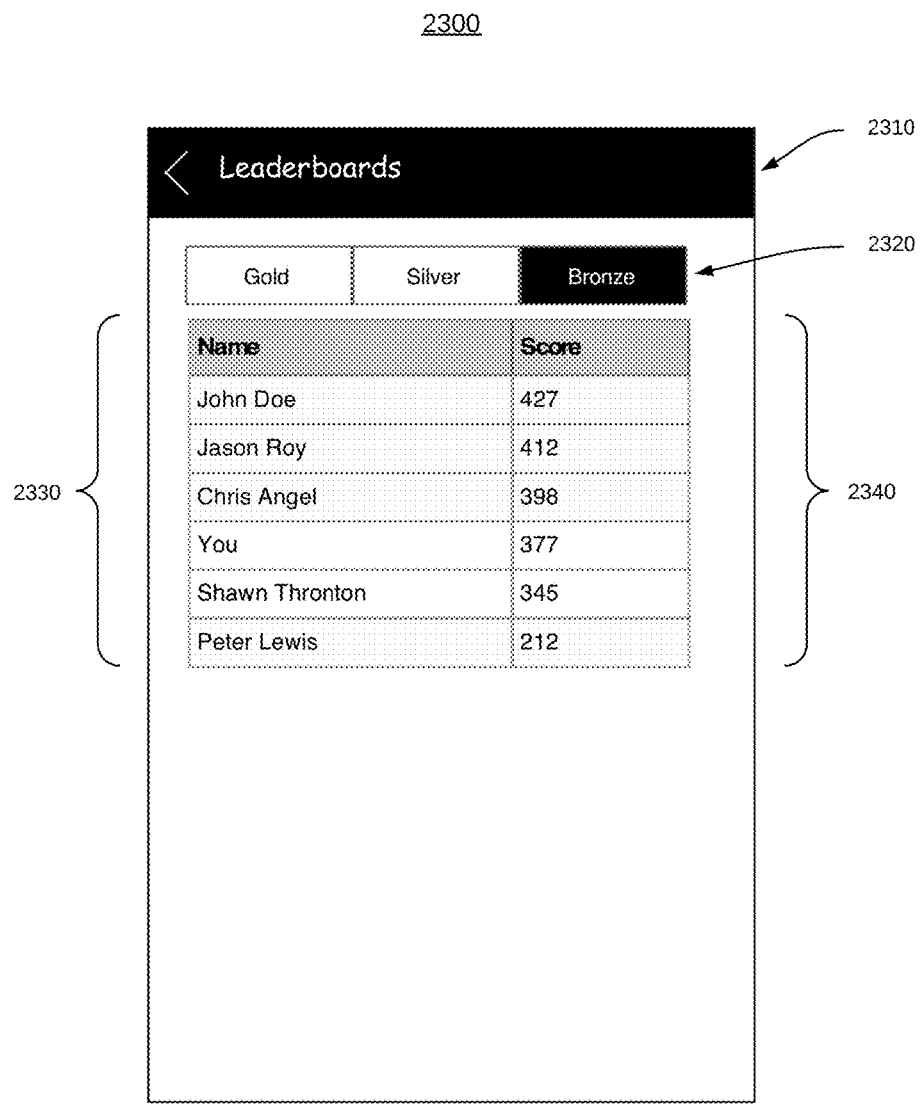
FIG. 23 is an illustrative figure showing a social gamification community Leader Board, according to one embodiment of the present invention.
Figure 24A:
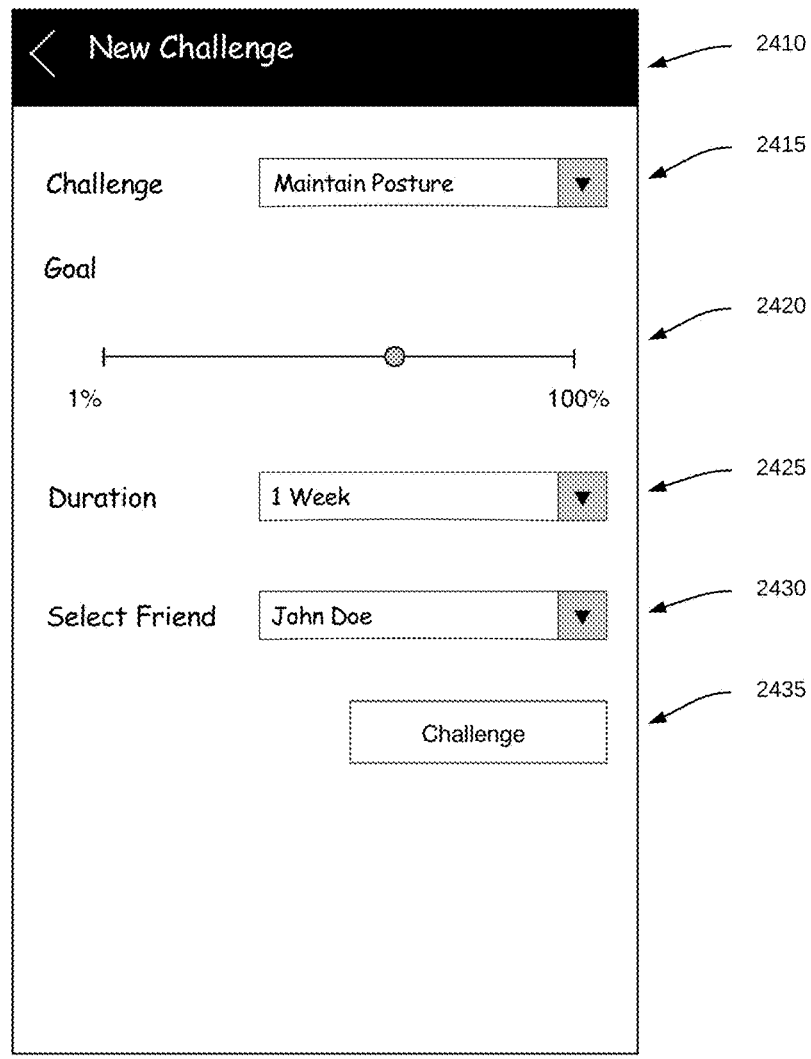
FIG. 24A is an illustrative figure showing a setup page for a new challenge, according one embodiment of the present invention.
Figure 24B:
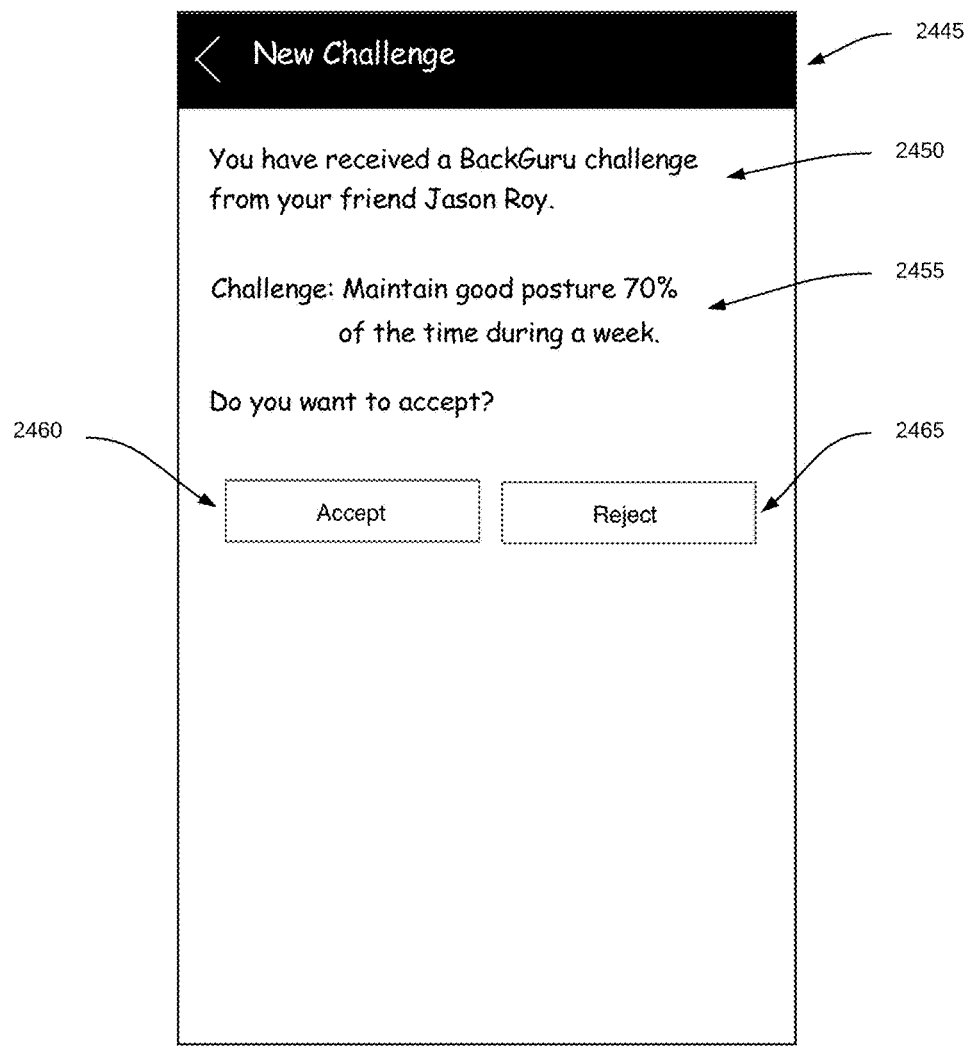
FIG. 24B is an illustrative figure showing a challenge invite page, according to one embodiment of the present invention.
Figure 24C:
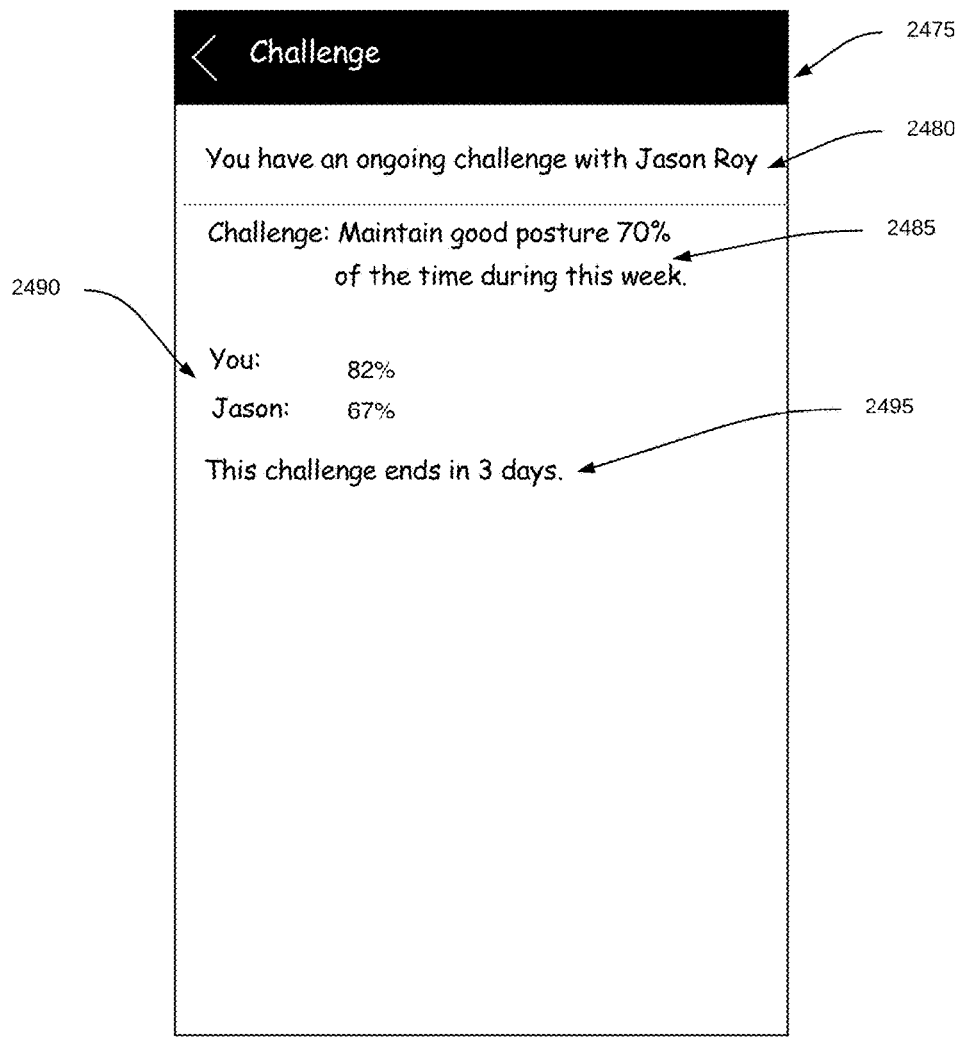
FIG. 24C is an illustrative figure showing an ongoing challenge status page, according to one embodiment of the present invention.
Figure 25:
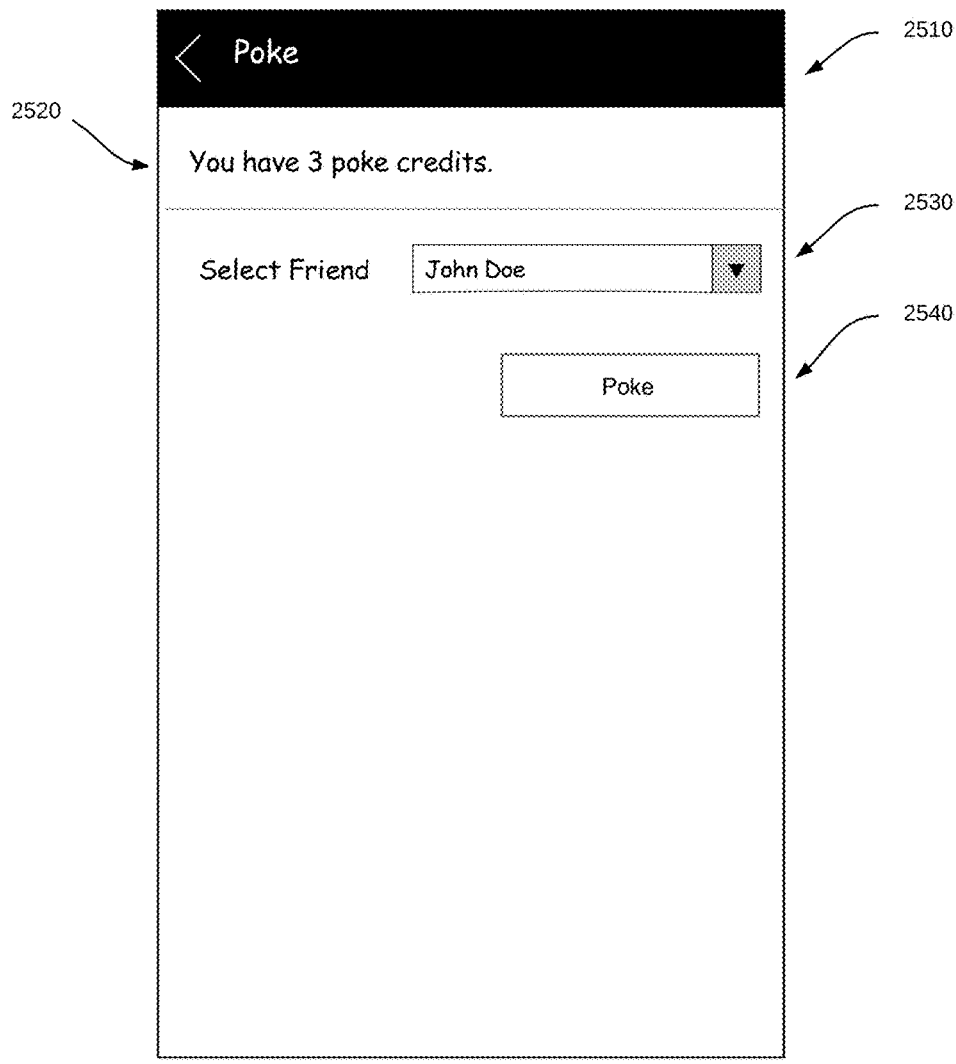
FIG. 25 is an illustrative figure showing a poke page, according to one embodiment of the present invention.

FIG. 23 through FIG. 25 are illustrative screen captures of a user device showing gamification and social features, according to some embodiments of the present invention, respectively. FIG. 23 is an illustrative screen capture 2300 showing a social gamification community Leader Board. A display title bar 2310 shows that the Leader Boards page is being viewed. In a tier field 2320, the user has selected to view people in the Bronze tier. Other available options in this example are Gold and Silver. Names 2330 of individuals in the Bronze tier are listed along with corresponding scores 2340 in a descending numerical order. Other tier classification schemes and structures are also possible in other embodiments of the present invention.

In some embodiments, users may challenge their friends with a postural goal. The user who wins the challenge may receive "poke" credits, where each "poke" credit may allow a user to poke a friend via, for example, a vibration, using a notification device built in the friends' smart seat cover system.

FIG. 24A through FIG. 24C outline the process of creating and maintaining a challenge. FIG. 24A is an illustrative screen capture 2400 of a user device or an application interface, showing a setup page for a new challenge, according to one embodiment of the present invention. A display title 2410 shows that a new challenge is being created. A challenge type selection menu 2415 may allow the user to select a type for the new challenge. For example, the user may elect to maintain a correct posture, or correct an incorrect posture over a configurable period of time. A percentage selection menu 2420 may allow the user to select a minimum percentage of correct sitting time which users involved in the challenge should attain in order to meet the challenge over a duration as set through a menu 2425. A challenge may be set for a day, a week, a month, a few months, or some other periods of time as may be selected from a calendar. A friend selection menu 2430 may allow the user to select a friend to challenge. In some embodiments, a group challenge may be possible. The user may complete setting up a new challenge by clicking on a challenge submit button 2435.

FIG. 24B is an illustrative FIG. 2440 showing a challenge invite page, according to one embodiment of the present invention. A display title 2445 "New Challenge" shows that this is a page about a new challenge. A challenge invite message 2450 may inform the receiving user of the challenger who has sent the invite. A challenge content message 2455 may inform the user of the goal for the challenge. The user may accept the new challenge invite by clicking on an accept button 2460 or decline it by clicking on a reject button 2465.

FIG. 24C is an illustrative FIG. 2470 showing an ongoing challenge status page, according to one embodiment of the present invention. The display title 2475 "Challenge" shows that this pages details an ongoing challenge. An ongoing challenge message 2480 "You have an ongoing challenge with Jason Ray" may remind the user of participants in the ongoing challenge. A challenge content message 2485 "Challenge: Maintain good posture 70% of the time during a week" may remind the user of the content of the ongoing challenge. A challenge status 2490 shows the percentages of time for which each user involved in the challenge has maintained a good posture. Finally, a challenge countdown message 2495 "This challenge ends in 3 days" may motivate the user to keep up a current good status, or to improve posture more often to attain the goal for the challenge.

FIG. 25 is an illustrative FIG. 2500 showing a poke page, according to one embodiment of the present invention. The display title 2510 "Poke" shows that this is a poke page, and the poke privilege status 2520 displays a statement "You have 3 poke credits" informs the user of how many friend poke privileges remain. A friend selection drop-down menu 2530 allows the user to select a friend to poke, and the user may complete the poking process by clicking on a poke submit button 2540. Gamification features described herein may make posture monitoring a more fun process, for the user to participate and improve over time.

Implementation of the Present Invention

Figure 26:
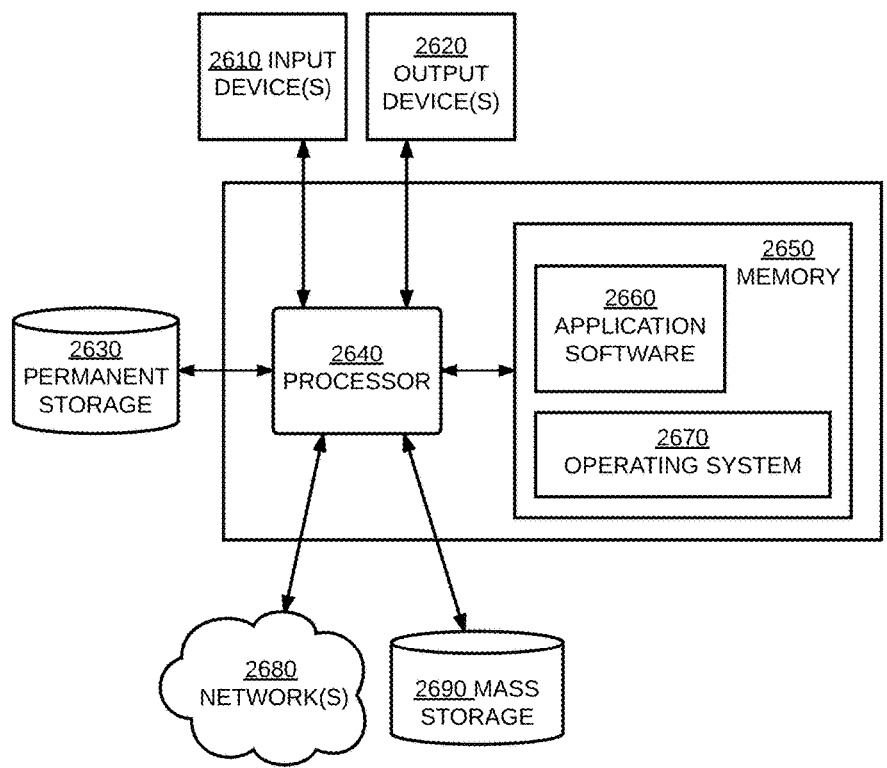
FIG. 26 is an illustrative hardware architecture diagram of a server for implementing one embodiment of the present invention.

The present invention may be implemented using server-based hardware and software. FIG. 26 shows an illustrative hardware architecture diagram 2600 of a server for implementing one embodiment of the present invention.

The present invention may be implemented in hardware and/or in software. Many components of the system, for example, network interfaces etc., have not been shown, so as not to obscure the present invention. However, one of ordinary skill in the art would appreciate that the system necessarily includes these components. A user-device is a hardware that includes at least one processor 2640 coupled to a memory 2650. The processor may represent one or more processors (e.g., microprocessors), and the memory may represent random access memory (RAM) devices comprising a main storage, as well as any supplemental levels of memory e.g., cache memories, non-volatile or back-up memories (e.g. programmable or flash memories), read-only memories, etc. In addition, the memory may be considered to include memory storage physically located elsewhere in the hardware, e.g. any cache memory in the processor, as well as any storage capacity used as a virtual memory, e.g., as stored on a mass storage device.

The hardware of a user device also typically receives a number of inputs 2610 and outputs 2620 for communicating information externally. For interface with a user, the hardware may include one or more user input devices (e.g., a keyboard, a mouse, a scanner, a microphone, a web camera, etc.) and a display (e.g., a Liquid Crystal Display (LCD) panel). For additional storage, the hardware may also include one or more mass storage devices 2690, e.g., a floppy or other removable disk drive, a hard disk drive, a Direct Access Storage Device (DASD), an optical drive (e.g. a Compact Disk (CD) drive, a Digital Versatile Disk (DVD) drive, etc.) and/or a tape drive, among others. Furthermore, the hardware may include an interface to one or more external databases 2630, as well as one or more networks 2680 (e.g., a local area network (LAN), a wide area network (WAN), a wireless network, and/or the Internet among others) to permit the communication of information with other computers coupled to the networks. It should be appreciated that the hardware typically includes suitable analog and/or digital interfaces to communicate with each other.

The hardware operates under the control of an operating system 2670, and executes various computer software applications 2660, components, programs, codes, libraries, objects, modules, etc. indicated collectively by reference numerals to perform the methods, processes, and techniques described above.

Figure 27:
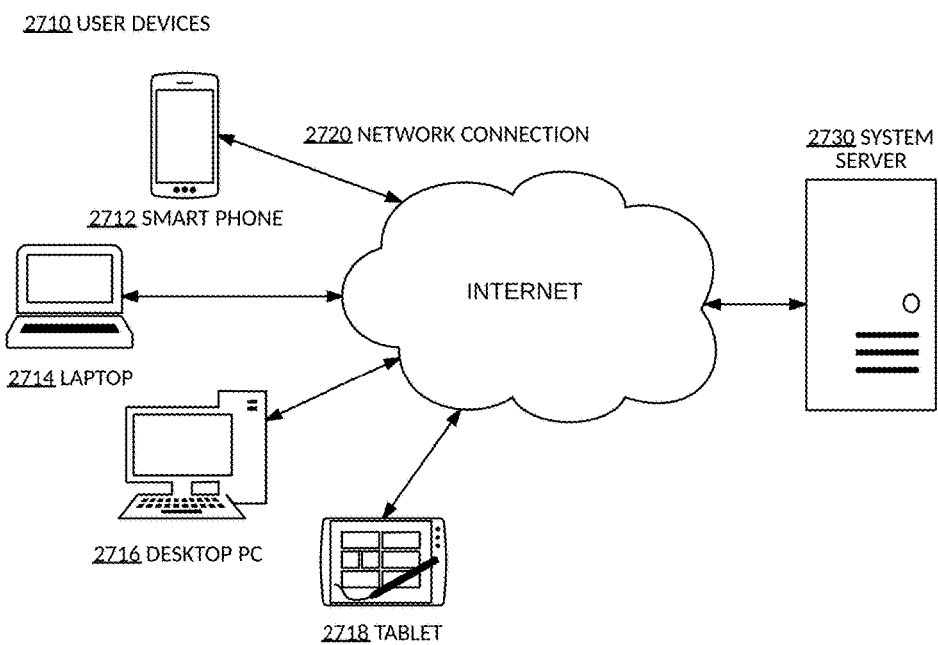
FIG. 27 is an illustrative system architecture for implementing one embodiment of the present invention in a client server environment.

The present invention may be implemented in a client server environment. FIG. 27 shows an illustrative system architecture 2700 for implementing one embodiment of the present invention in a client server environment. User devices 2710 on the client side may include smart phones 2712, laptops 2714, desktop PCs 2716, tablets 2718, or other devices. Such user devices 2710 access the service of the system server 2730 through some network connection 2720, such as the Internet. System server 2730 may serve the same functions as cloud server 285 shown in FIG. 2.

In some embodiments of the present invention, the entire system can be implemented and offered to the end-users and operators over the Internet, in a so-called cloud implementation. No local installation of software or hardware would be needed, and the end-users and operators would be allowed access to the systems of the present invention directly over the Internet, using either a web browser or similar software on a client, which client could be a desktop, laptop, mobile device, and so on. This eliminates any need for custom software installation on the client side and increases the flexibility of delivery of the service (software-as-a-service), and increases user satisfaction and ease of use. Various business models, revenue models, and delivery mechanisms for the present invention are envisioned, and are all to be considered within the scope of the present invention.

In general, the method executed to implement the embodiments of the invention, may be implemented as part of an operating system or a specific application, component, program, object, module or sequence of instructions referred to as "computer program(s)" or "computer code(s)." The computer programs typically comprise one or more instructions set at various times in various memory and storage devices in a computer, and that, when read and executed by one or more processors in a computer, cause the computer to perform operations necessary to execute elements involving the various aspects of the invention. Moreover, while the invention has been described in the context of fully functioning computers and computer systems, those skilled in the art will appreciate that the various embodiments of the invention are capable of being distributed as a program product in a variety of forms, and that the invention applies equally regardless of the particular type of machine or computer-readable media used to actually effect the distribution. Examples of computer-readable media include but are not limited to recordable type media such as volatile and non-volatile memory devices, floppy and other removable disks, hard disk drives, optical disks, Compact Disk Read-Only Memory (CD ROMS), Digital Versatile Disks, (DVDs), Flash Drives, Secure Digital (SD) Cards, and digital and analog communication media.

CONCLUSIONS

One of ordinary skill in the art knows that the use cases, structures, schematics, and flow diagrams may be performed in other orders or combinations, but the inventive concept of the present invention remains without departing from the broader scope of the invention. Every embodiment may be unique, and methods/steps may be either shortened or lengthened, overlapped with the other activities, postponed, delayed, and continued after a time gap, such that every user is accommodated to practice the methods of the present invention.

Although the present invention has been described with reference to specific exemplary embodiments, it will be evident that the various modification and changes can be made to these embodiments without departing from the broader scope of the invention. Accordingly, the specification and drawings are to be regarded in an illustrative sense rather than in a restrictive sense. It will also be apparent to the skilled artisan that the embodiments described above are specific examples of a single broader invention which may have greater scope than any of the singular descriptions taught. There may be many alterations made in the descriptions without departing from the scope of the present invention.

What is claimed is:

1. A system for monitoring and correcting sitting posture of a user, and for discouraging sedentary behavior of the user, comprising:
    a processor operatively connected to a clock;
    a portable seat cover comprising a backrest portion and a seat portion, adapted for attachment to a chair;
    a plurality of sensors embedded in the portable seat cover and each operatively connected to the processor, including at least three pressure sensors embedded in the backrest portion for monitoring shoulder and lower back positions of the user, at least one angle sensor embedded in the backrest portion for monitoring an inclination of the backrest portion relative to the seat portion, and at least two pressure sensors embedded in the seat portion for monitoring leg positions of the user;
    a notification device attached to the portable seat cover and operatively connected to the processor;
    a non-transitory physical storage medium for storing program code and operatively connected to the processor, the program code when executed by the processor causes the processor to:
        initiate an idleness timer to count how long the user has been sitting, wherein the idleness timer is activated when the user sits on the seat portion of the portable seat cover, and deactivated when the user stands up from sitting on the seat portion of the portable seat cover;

monitor the user's sitting posture by receiving, at discrete intervals in real-time, a first plurality of sensor measurement values from the plurality of sensors;

identify a sitting posture of the user by applying a posture identification rule to the first plurality of sensor measurement values, wherein the posture identification rule is based on the user's weight;

determine whether the sitting posture is ergonomically correct by identifying a category that the sitting posture belongs to;

in response to determining that the sitting posture is not ergonomically correct, generate a posture correction notification through the notification device to alert the user to correct the sitting posture;

determine whether a sedentary threshold has been reached by comparing the idleness timer to the sedentary threshold;

in response to determining that the sedentary threshold has been reached, generate a stand notification through the notification device to alert the user to stand up;

initiate a stand timer to count how long the user has been standing, wherein the stand timer is activated when the user stands up from sitting on the seat portion of the portable seat cover, and deactivated when the user sits on the seat portion of the portable seat cover;

determine whether the user has stood up in response to the stand notification;

in response to determining that the user has not stood up in response to the stand notification, reduce the idleness timer by a predetermined amount of time;

in response to determining that the user has stood up in response to the stand notification, pause the idleness timer until the user is seated again, increase the stand timer by the amount of time the user stood, and determine whether a standing time threshold has been reached by comparing the stand timer to the standing time threshold;

in response to determining that the standing time threshold has been reached, reset the idleness timer and the stand timer; and in response to determining that the standing time threshold has not been reached, reduce the idleness timer by a predetermined amount of time and reset the stand timer.

2. The system of claim 1, wherein the plurality of sensors comprises at least four pressure sensors embedded in the seat portion for monitoring leg positions of the user.

3. The system of claim 1, wherein the stand notification comprises an action selected from the group consisting of making the seat uncomfortable to sit in, and generating a reminder alert for display on a user device.

4. The system of claim 1, wherein the posture correction notification comprises actions selected from the group consisting of poking the user at one or more locations on the portable seat cover, vibrating a portion of the portable seat cover, generating a reminder alert for display on a user device, generating sitting posture information for display on the user device, and sending a notification to the user device.

5. The system of claim 1, wherein the program code when executed by the processor, further causes the processor to:
receive height and weight information of the user; and
calibrate the system by:
instructing the user to sit in a calibration posture, and receiving a plurality of calibration sensor measurement values from the plurality of sensors, wherein the posture identification rule is based on the plurality of calibration sensor measurement values.

6. The system of claim 1, wherein the program code when executed by the processor, further causes the processor to:
generate, for display on a user device, sitting posture information based on the first plurality of sensor measurement values, wherein the sitting posture information indicates whether one or more sensors are measuring values within an ergonomic range;
receive a second plurality of sensor measurement values from the plurality of sensors;
determine whether a posture change has occurred by comparing the second plurality of sensor measurement values to the first plurality of sensor measurement values; and
in response to determining that a posture change has occurred, generate, for display on a user device, updated sitting posture information based on the second plurality of sensor measurement values.

7. The system of claim 1, wherein the program code when executed by the processor, further causes the processor to:
timestamp the first plurality of sensor measurement values and the identified sitting posture; and
send the timestamped first plurality of sensor measurement values and/or the timestamped sitting posture to a user device, wherein the user device later uploads the time stamped first plurality of sensor measurements values and/or the timestamped sitting posture to a cloud server, when an upload connection becomes available.

8. The system of claim 1, further comprising a user device having access to the processor, wherein the user device performs a social gamification function selected from the group consisting of causing the processor to generate a posture correction notification in response to receiving a poke request from a friend, updating a posture challenge score according to the sitting posture, uploading time-stamped historical posture data received from the processor to a community database, and causing the processor to update the sedentary threshold based on a group goal or a peer-to-peer goal received from the community database.

9. The system of claim 1, wherein the program code when executed by the processor, further causes the processor to identify a stress level of the user based on sitting posture movement patterns.

10. A method for monitoring and correcting sitting posture of a user, and for discouraging sedentary behavior of the user, comprising:
initiating an idleness timer to count how long the user has been sitting,
wherein the idleness timer is activated when the user sits on a seat portion of a portable seat cover, and deactivated when the user stands up from sitting on the seat portion of the portable seat cover,
wherein the portable seat cover comprises a backrest portion and a seat portion, adapted for attachment to a chair,
wherein the portable seat cover comprises a plurality of embedded sensors each operatively connected to a processor, including at least three pressure sensors embedded in the backrest portion for monitoring shoulder and lower back positions of the user, at least one angle sensor embedded in the backrest portion for monitoring an inclination of the backrest portion relative to the seat portion, and at least two pressure sensors embedded in the seat portion for monitoring leg positions of the user;

monitoring the user's sitting posture by receiving, at discrete intervals in real-time, a first plurality of sensor measurement values from the plurality of sensors;

identifying a sitting posture of the user by applying a posture identification rule to the first plurality of sensor measurement values, wherein the posture identification rule is based on the user's weight;

determining whether the sitting posture is ergonomically correct by identifying a category that the sitting posture belongs to;

in response to determining that the sitting posture is not ergonomically correct, generating a posture correction notification through the notification device to alert the user to correct the sitting posture;

determining whether a sedentary threshold has been reached by comparing the idleness timer to the sedentary threshold;

in response to determining that the sedentary threshold has been reached, generating a stand notification through the notification device to alert the user to stand up;

initiating a stand timer to count how long the user has been standing, wherein the stand timer is activated when the user stands up from sitting on the seat portion of the portable seat cover, and deactivated when the user sits on the seat portion of the portable seat cover;

determining whether the user has stood up in response to the stand notification;

in response to determining that the user has not stood up in response to the stand notification, reducing the idleness timer by a predetermined amount of time;

in response to determining that the user has stood up in response to the stand notification, pausing the idleness timer until the user is seated again, increasing the stand timer by the amount of time the user stood, and determining whether a standing time threshold has been reached by comparing the stand timer to the standing time threshold;

in response to determining that the standing time threshold has been reached, resetting the idleness timer and the stand timer; and in response to determining that the standing time threshold has not been reached, reducing the idleness timer by a predetermined amount of time and reset the stand timer.

11. The method of claim 10, wherein the plurality of sensors comprises at least four pressure sensors embedded in the seat portion for monitoring leg positions of the user.

12. The method of claim 10, wherein the posture correction notification comprises an action selected from the group consisting of poking the user at one or more locations on the portable seat cover, vibrating a portion of the portable seat cover, generating a reminder alert for display on a user device, generating sitting posture information for display on the user device, and sending a notification to the user device.

13. The method of claim 10, further comprising:
generating, for display on a user device, sitting posture information based on the first plurality of sensor measurement values, wherein the sitting posture information indicates whether one or more sensors are measuring values within an ergonomic range;

receiving a second plurality of sensor measurement values from the plurality of sensors;

determining whether a posture change has occurred by comparing the second plurality of sensor measurement values to the first plurality of sensor measurement values; and in response to determining that a posture change has occurred, generating, for display on a user device, updated sitting posture information based on the second plurality of sensor measurement values.

14. The method of claim 10, further comprising a gamification functions selected from the group consisting of:
causing the processor to generate a posture correction notification in response to receiving a poke request from a friend, updating a posture challenge score according to the sitting posture, uploading timestamped historical posture data to a community database, and updating the sedentary threshold based on a group goal or a peer-to-peer goal received from the community database.

15. A non-transitory computer-readable storage medium for monitoring and correcting sitting posture of a user, and for discouraging sedentary behavior of the user, the storage medium comprising program code stored thereon, that when executed by a processor, causes the processor to:

initiate an idleness timer to count how long the user has been sitting,
wherein the idleness timer is activated when the user sits on the seat portion of a portable seat cover, and deactivated when the user stands up from sitting on the seat portion of the portable seat cover,
wherein the portable seat cover comprises a backrest portion and a seat portion, adapted for attachment to a chair,
wherein the portable seat cover comprises a plurality of embedded sensors each having access to a processor, including at least three pressure sensors embedded in the backrest portion for monitoring shoulder and lower back positions of the user, at least one angle sensor embedded in the backrest portion for monitoring an inclination of the backrest portion relative to the seat portion, and at least two pressure sensors embedded in the seat portion for monitoring leg positions of the user;

monitor the user's sitting posture by receiving, at discrete intervals in real-time, a first plurality of sensor measurement values from the plurality of sensors;

identify a sitting posture of the user by applying a posture identification rule to the first plurality of sensor measurement values, wherein the posture identification rule is based on the user's weight;

determine whether the sitting posture is ergonomically correct by identifying a category that the sitting posture belongs to;

in response to determining that the sitting posture is not ergonomically correct, generate a posture correction notification through the notification device to alert the user to correct the sitting posture;

determine whether a sedentary threshold has been reached by comparing the idleness timer to the sedentary threshold;

in response to determining that the sedentary threshold has been reached, generate a stand notification through the notification device to alert the user to stand up;

initiate a stand timer to count how long the user has been standing, wherein the stand timer is activated when the user stands up from sitting on the seat portion of the portable seat cover, and deactivated when the user sits on the seat portion of the portable seat cover;

determine whether the user has stood up in response to the stand notification;

in response to determining that the user has not stood up in response to the stand notification, reduce the idleness timer by a predetermined amount of time;

in response to determining that the user has stood up in response to the stand notification, pause the idleness timer until the user is seated again, increase the stand timer by the amount of time the user stood, and determine whether a standing time threshold has been reached by comparing the stand timer to the standing time threshold;

in response to determining that the standing time threshold has been reached, reset the idleness timer and the stand timer;

in response to determining that the standing time threshold has not been reached, reduce the idleness timer by a predetermined amount of time and reset the stand timer;

initiate a stand timer to count how long the user has been standing, wherein the stand timer is activated when the user stands up from sitting on the seat, and deactivated when the user sits on the seat;

determine whether the user has stood up in response to the stand notification;

in response to determining that the user has not stood up in response to the stand notification, reduce the idleness timer by a predetermined amount of time;

in response to determining that the user has stood up in response to the stand notification, pause the idleness timer until the user is seated again, increase the stand timer by the amount of time the user stood, and determine whether a standing time threshold has been reached by comparing the stand timer to the standing time threshold;

in response to determining that the standing time threshold has been reached, reset the idleness timer and the stand timer; and in response to determining that the standing time threshold has not been reached, reduce the idleness timer by a predetermined amount of time and reset the stand timer.

16. The non-transitory computer-readable storage medium of claim 15, wherein the posture correction notification comprises an action selected from the group consisting of poking the user at one or more locations on the portable seat cover, vibrating a portion of the portable seat cover, generating a reminder alert for display on a user device, generating sitting posture information for display on the user device, and sending a notification to the user device.

17. The non-transitory computer-readable storage medium of claim 15, the storage medium further comprising program code that when executed by a processor, causes the processor to:

generate, for display on a user device, sitting posture information based on the first plurality of sensor measurement values, wherein the sitting posture information indicates whether one or more sensors are measuring values within an ergonomic range;

receive a second plurality of sensor measurement values from the plurality of sensors;

determine whether a posture change has occurred by comparing the second plurality of sensor measurement values to the first plurality of sensor measurement values; and in response to determining that a posture change has occurred, generate, for display on a user device, updated sitting posture information based on the second plurality of sensor measurement values.

* * * * *